US007566691B2

(12) United States Patent
Nestor

(10) Patent No.: US 7,566,691 B2
(45) Date of Patent: Jul. 28, 2009

(54) VASOACTIVE INTESTINAL POLYPEPTIDE PHARMACEUTICALS

(75) Inventor: John Nestor, Encinitas, CA (US)

(73) Assignee: Transition Therapeutics, Inc., Toronto, Ontario (CA)

( * ) Notice: Subject to any disclaimer, the term of this patent is extended or adjusted under 35 U.S.C. 154(b) by 216 days.

(21) Appl. No.: 11/245,499

(22) Filed: Oct. 7, 2005

(65) Prior Publication Data

US 2006/0079456 A1    Apr. 13, 2006

Related U.S. Application Data

(60) Provisional application No. 60/617,500, filed on Oct. 8, 2004.

(51) Int. Cl.
*A61K 38/00* (2006.01)
*A61K 38/12* (2006.01)
*C07K 17/00* (2006.01)

(52) U.S. Cl. .................. 514/2; 514/9; 514/12; 514/866; 530/317; 530/324

(58) Field of Classification Search ................ 514/2, 514/9, 12, 866; 530/317, 324
See application file for complete search history.

(56) References Cited

U.S. PATENT DOCUMENTS

| 4,757,133 A | 7/1988 | Ito et al. |
| 5,589,452 A | 12/1996 | Krstenansky et al. |
| 2004/0058870 A1 | 3/2004 | Froland et al. |
| 2005/0043237 A1 | 2/2005 | Pan et al. |
| 2005/0075290 A1 | 4/2005 | Ghandi |
| 2006/0079456 A1 | 4/2006 | Nestor |
| 2006/0234933 A1 | 10/2006 | Nestor |
| 2007/0293429 A1 | 12/2007 | Nestor |
| 2008/0214440 A1 | 9/2008 | Nestor |

FOREIGN PATENT DOCUMENTS

| MX | PA04012305 | 2/2005 |
| WO | WO 01/23420 | 4/2001 |
| WO | WO 01/23420 A2 * | 4/2001 |
| WO | WO-03-096024 | 11/2003 |
| WO | WO-2004-006839 A2 | 1/2004 |
| WO | WO-2005-089229 | 9/2005 |
| WO | WO-2005-113593 A1 | 12/2005 |
| WO | WO-2005-113594 | 12/2005 |
| WO | WO-2005-123109 | 12/2005 |
| WO | WO-2005-023356 A2 | 3/2006 |
| WO | WO-2006-023358 A1 | 3/2006 |
| WO | WO-2006-023359 A2 | 3/2006 |
| WO | WO-2006-023367 A1 | 3/2006 |
| WO | WO 2006/042152 | 4/2006 |
| WO | WO 2007/044591 | 4/2007 |
| WO | WO 2008/043102 | 4/2008 |

OTHER PUBLICATIONS

Cornette, D.B. et al. "Hydrophobicity Scales and Computational Techniques for Detecting Amphipathic Structures in Proteins," J. Mol. Biol. 195:659-685 (1987).

Eisenberg, D. et al., "The helical hydrophobic moment: a measure of the amphiphilicity of a helix," Nature 299:371-374 (1982).

Eisenberg, D. et al., "The hydrophobic moment detects periodicity in protein hydrophobicity," PNAS USA 81:140-144 (1984).

Filipsson, K. et al., "Pituitary Adenylate Cyclase-Activating Polypeptide Stimulates Insulin and Glucagon Secretion in Humans," J. Clin. Endocrinol. Metab. 82:3093-3098 (1977).

Krstenansky, J.L. et al., "Short model peptides having a high α-helical tendency: design and solution properties ," FEBS Ltrs. 242(2):409-413 (1989).

Schiffer, M. and Edmundson, A.B., "Use of helical wheels to represent the structures of proteins and to identify segments with helical potential," Biophys. J. 7:121-135 (1967).

Segrest, J.P. et al., "Amphipathic Helix Motif: Classes and Properties," Proteins: Structure, Function and Genetics 8:103-117 (1990).

Sweet, I.R. et al., "Systematic screening of potential β-cell imaging agents," Biochem. Biophys. Res. Commun. 314:976-983 (2004).

Corry, D.B. and Kheradmand, F., "Control of allergic airway inflammation through immunomodulation," J. Allergy Clin. Immunol. 117 (2 Suppl.):S461-47 (2006).

Das, D.K. et al., "Coordinated Role of Vasoactive Intestinal Peptide and Nitric Oxide in Cardioprotection," Ann. NY Acad. Sci. 865:297-308 (1998).

Dawson, P.E. et al., "Synthesis of Proteins by Native Chemical Ligation," Science 266:776-9 (1994).

Erdelyi, M. and Gogoll, A., "Rapid Microwave-Assisted Solid Phase Peptide Synthesis," Synthesis 1592-6 (2002).

Haj, R.M. et al., "Treatment of pulmonary hypertension with selective pulmonary vasodilators," Curr. Opin. Anesthesiol. 19:88-95 (2006).

Kalfin, R. et al., "Protective Role of Intracoronary Vasoactive Intestinal Peptide in Ischemic and Reperfused Myocardium," J. Pharmacol. Exp. Ther. 268:952-8 (1994).

Levy, J.H., "Management of Systemic and Pulmonary Hypertension," Tex. Heart Inst. J. 32:467-71 (2005).

(Continued)

*Primary Examiner*—Jon P Weber
*Assistant Examiner*—Abdel A Mohamed
(74) *Attorney, Agent, or Firm*—Howson & Howson LLP

(57) ABSTRACT

Pharmaceutical compositions relating to vasoactive intestinal polypeptides and methods for the treatment of metabolic disorders, including diabetes, insulin resistance, metabolic acidosis and obesity are presented. Methods of using the vasoactive intestinal polypeptide compositions are also disclosed.

9 Claims, 4 Drawing Sheets

OTHER PUBLICATIONS

Linden, A. et al., "Bronchodilation by an inhaled VPAC2 receptor agonist in patients with stable asthma," Thorax 58:217-21 (2003).

Mandal, T.K., "Inhaled insulin for diabetes mellitus," Am. J. Health Syst. Pharm. 62:1359-64 (2005).

Moreno, D. et al., "Development of selective agonists and antagonists for the human vasoactive intestinal polypeptide VPAC2 receptor," Peptides 21:1543-9 (2000).

Nestor, J.J. Jr., "Improved Duration of Action of Peptide Drugs," In *Peptide-based Drug Design*: Taylor MD, Amidon GL, eds.; American Chemical Society Washington DC, 1995:449-471.

Nilsson, B.L. et al., "Chemical Synthesis of Proteins," Annu. Rev. Biophys. Biomol. Struct. 34:91-118 (2005).

Petkov, V. et al., "Vasoactive intestinal peptide as a new drug for treatment of primary pulmonary hypertension," J. Clin. Invest. 111:1339-46 (2003).

Pfutzner, A. and Forst, T.E., "Pulmonary insulin delivery by means of the Technosphere™ drug carrier mechanism," Expert Opin. Drug Deliv. 2(6):1097-106 (2005).

Rucker, A.L. et al., "Host-Guest Scale of Left-Handed Polyproline II Helix Formation," Proteins 53:68-75 (2003).

Stapley, B.J. and Creamer, T.P., "A survey of left-handed polyproline II helices," Protein Sci. 8:587-95 (1999).

Vaudry, D. et al., "Pituitary Adenylate Cyclase-Activating Peptide and Its Receptors: From Structure to Functions," Pharmacol. Rev. 52:269-324 (2000).

Arnold, J.J. et al., "Correlation of Tetradecylmaltoside Induced Increases in Nasal Peptide Drug Delivery with Morphological Changes in Nasal Epithelial Cells," J. Pharm. Sci. 93, pp. 2205-2213 (2004).

Deiters, A. et al., "Site-Specific PEGylation of Proteins Containing Unnatural Amino Acids," Bio-org. Med. Chem. Lett. 14, pp. 5743-5745 (2004).

Gourlet, P. et al., "Interaction of Lipophilic VIP Derivatives with Recombinant VIP1/PACAP and VIP2/PACAP Receptors," Eur. J. Pharm. 354, pp. 105-111 (1998).

Gourlet, P. et al., "The Long-Acting Vasoactive Intestinal Polypeptide Agonist RO 25-1553 is Highly Selective of the VIP2 Receptor Subclass," Peptides 18, pp. 403-408 (1997).

Greenwald, R. B. et al., "Effective Drug Delivery by PEGylated Drug Conjugates," Adv. Drug Del. Rev. 55, pp. 217-250 (2003).

Keiffer, T.J. and Habener, J.R., "The Glucogen-Like Peptides," Endocr. Rev. 20, pp. 876-913 (1999).

Knudsen, L.B., "Glucagon-Like Peptide-1: The Basis of a New Class of Treatment for Type 2 Diabetes," J. Med. Chem. 47, pp. 4128-4134 (2004).

Knudsen, L.B. et al., "Potent Derivatives of Glucagon-Like Peptide-1 with Pharmacokinetic Properties Suitable for Once Daily Administration," J. Med. Chem. 43, pp. 1664-1669 (2000).

Kurtzhals, P. et al., "Engineering Predictability and Protraction in a Basal Insulin Analogue: The Pharmacology of Insulin Detemir," Int. J. Obesity 28, Supp. 2, pp. S23-28 (2004).

Kurtzhals, P. et al., "Albumin Binding of Insulins Acylated with Fatty Acids: Characterization of the Ligand-Protein Interaction and Correlation Between Binding Affinity and Timing of the Insulin Effect in vivo," Biochem. J., 312, pp. 725-731 (1995).

Langer, I. et al., "Hexanoylation of VPAC2 Receptor-Preferring Ligand Markedly Increased Its Selectivity and Potency," Peptides 25:275-8 (2004).

Nielsen, L.L. et al., "Pharmacology of Exenatide (synthetic exendin-4): A Potential Therapeutic for Improved Glycemic Control of Type 2 Diabetes," Regul. Peptides 117, pp. 77-88 (2004).

Tsutsumi, M. et al., "A Potent and Highly Selective VPAC2 Agonist Enhances Glucose-Induced Insulin Release and Glucose Disposal. A Potential Therapy for Type 2 Diabetes," Diabetes 51:1453-60 (2002).

Xia, M. et al., "Novel Cyclic Peptide Agonist of High Potency and Selectivity for the Type II Vasoactive Intestinal Peptide Receptor," J. Pharm. Exp. Ther. 281, pp. 629-633 (1997).

Yung, S.L. et al., "Generation of Highly Selective VPAC2 Receptor Agonists by High Throughput Mutagenesis of Vasoactive Intestinal Polypeptide and Pituitary Adenylate Cyclase-Activating Peptide," J. Biol. Chem. 278:10273-10281 (2003).

Gololobov, G. et al., "Stabilization of Vasoactive Intestinal Peptide by Lipids," J. of Pharmacology and Experimental Therapeutics 285:753-758 (1998).

Rubenstein, I. et al., "Conformation and vasoreactivity of VIP in phospholipids: effects of calmodulin," Peptides 20:1497-1501 (1999).

Yeomans, D.C. et al., "Conformation-dependent effects of VIP on nociception in rats," Peptides 24:617-622 (2003).

Thiyagarajan, "A predicted amphipathic helix mediates plasma membrane localization of GRK5", The Journal of Biological Chemistry, vol. 279, No. 17, (Apr. 23, 2004: Epub Feb. 19, 2004) pp. 17989-17995.

* cited by examiner

FIG. 1A

| Sequence Identifier | Name | Amino Acid Sequence |
|---|---|---|
| SEQ ID NO: 1 | TP-100 | pen H S D A V F T D N Y T R L R K Q V A A K K Y L N W I K K A K R E L L E K L Z |
| SEQ ID NO: 2 | TP-103 | pen H S D A V F T D N Y T R L R K Q V A A K K Y L N S I K K G K R E L L E K L L R K L Z lau |
| SEQ ID NO: 3 | TP-104 | pen H S D A V F T D N Y T R L R K Q V A A K K Y L N S I K K G K R E L L E K L Z lau |
| SEQ ID NO: 4 | TP-105 | H S D A V F T D N Y T R L R K Q V A A K K Y L N S I K K G K R E L L E K L L R K L Z lau |
| SEQ ID NO: 5 | TP-106 | pen H S D A V F T D N Y T R L R K Q V A A K K Y L N S I K K G K R E L L E K L Z myr |
| SEQ ID NO: 6 | TP-107 | pen H S D A V F T D N Y T R L R K Q V A A K K Y L N W I K K A K R E L L E K L Z ste |
| SEQ ID NO: 7 | TP-108 | pen H S D A V F T D N Y T R L R K Q L A A K K Y L N S I K K G K R L L R K L Q P P P Z ste |
| SEQ ID NO: 8 | TP-1 | H S D A V F T D N Y T R L R K Q M A A K K Y L N S I K K G K R E L L E K L L R K L |
| SEQ ID NO: 9 | TP-2 | acyl H S D A V F T D N Y T R L R K Q M A A K K Y L N S I K K G K R E L L E K L L R K L P P P |
| SEQ ID NO: 10 | TP-3 | acyl H S D A V F T D N Y T R L R K Q M A A K K Y L N S I K K G K R E L L E K L L R K Z |
| SEQ ID NO: 11 | TP-4 | acyl H S D A V F T D N Y T R L R K Q M A A K K Y L N S I K K G K R E L L E R L L R K L |
| SEQ ID NO: 12 | TP-5 | acyl H S D A V F T D N Y T R L R K Q M A A K K Y L N S I K K G K R E L L E K L L R K L |

FIG. 1B

| Sequence Identifier | Name | Amino Acid Sequence |
|---|---|---|
| SEQ ID NO: 13 | TP-6 | H S D A V F T D N Y T R L R K Q M A A K K Y L N S I K K G K R E L L E K L L R K Z |
| SEQ ID NO: 14 | TP-7 | hex H S D A V F T D N Y T R L R K Q M A A K K Y L N S I K K G K R E L L E K L L R K L P P P |
| SEQ ID NO: 15 | TP-8 | hex H S D A V F T D N Y T R L R K Q M A A K K Y L N S I K K G K R E L L E R L L R K L (PEG4) |
| SEQ ID NO: 16 | TP-9 | hex H S D A V F T D N Y T R L R K Q M A A K K Y L N S I K K G K R E L L E K L L R K K (C12) |
| SEQ ID NO: 17 | TP-10 | H S D A V F T D N Y T R L R K Q M A A K K Y L N S I K K G K R E L L E K L L R K L P P P |
| SEQ ID NO: 18 | TP-11 | H S D A V F T D N Y T R L R K Q M A A K K Y L N S I K K G K R E L L E R L L R K L (PEG4) |
| SEQ ID NO: 19 | TP-12 | H S D A V F T D N Y T R L R K Q M A A K K Y L N S I K K G K R E L L E K L L R K K (C12) |
| SEQ ID NO: 20 | TP-201 | pen H S D A V F T D N Y T R L R K Q V A A K K Y L N S I K K A K R E L L E K L Z ste |
| SEQ ID NO: 21 | TP-202 | pen H S D A V F T R N Y T R L R R Q L A A R R Y L N S I K K A R R L L R L L P P P Z ste |
| SEQ ID NO: 22 | TP-203 | pen H S D A V F T R N Y T R L R R Q L A A R R Y L N S I K K A R R L L R L L Q P P P Z ste |
| SEQ ID NO: 23 | TP-205 | pen H S D A V F T D N Y T R L R K Q L A A K K Y L N S I K K G K R L L R K L Q P P P Z ste |
| SEQ ID NO: 24 | TP-206 | pen H S D A V F T D N Y T R L R K Q V A A K K Y L N S I K K G K R E L L E K L Z lau |

FIG. 1C

| Sequence Identifier | Name | Amino Acid Sequence |
|---|---|---|
| SEQ ID NO: 25 | TP-207 | pen H S D A V F T D N Y T R L R K Q V A A K K Y L N S I K K G K R E L L E K L Z myr P P P |
| SEQ ID NO: 26 | TP-301 | pen H S D A V F T R N Y T R L R R Q L A A R R Y L N S I K K A R R L L R R L Q P P P Z ste |
| SEQ ID NO: 27 | TP-302 | hex H S D A V F T R N Y T R L R R Q L A A R R Y L N S I K K A R R L L E K L L R K L Z ste |
| SEQ ID NO: 28 | TP-303 | pen H S D A V F T R N Y T R L R R Q L A A R R Y L N W I K K A R R L L E K L L R K L Z ste P P P |
| SEQ ID NO: 29 | TP-304 | pen H S D A V F T R N Y T R L R R Q L A A R R Y L N W I K K A R R E L L E K L L R K L Z ste |
| SEQ ID NO: 30 | TP-305 | pen H S D A V F T R N Y T R L R R Q L A A K K Y L N S I K K A R R L L E K L Z ste P P P |
| SEQ ID NO: 31 | TP-115 | pen H S D A V F T D N Y T R L R K Q V A A K K Y L N W I K K A K R E L L E K L Z ste |
| SEQ ID NO: 32 | TP-116 | pen H S D A V F T D N Y T R L R K Q V A A K K Y L N S I K K A K R E L L E K L Z ste |
| SEQ ID NO: 33 | TP-117 | acyl H S D A V F T D N Y T R L R K Q V A A K K Y L N W I K K A K R E L L E K L Z ste |
| SEQ ID NO: 34 | TP-118 | pr H S D A V F T D N Y T R L R K Q V A A K K Y L N W I K K A K R E L L E K L Z ste |
| SEQ ID NO: 35 | TP-119 | pen H S D A V F T D N Y T R L R K Q V A A K K Y L N W I K R A K R E L L E K L Z ste |
| SEQ ID NO: 36 | TP-120 | pen H S D A V F T D N Y T R L R K Q V A A K K Y L N W I K K G K R L L R K L G P P P Z ste |
| SEQ ID NO: 37 | TP-121 | pen H S D A V F T D N Y T R L R K Q V A A K K Y L N W I K K G K R L L R K L A P P P Z ste |
| SEQ ID NO: 38 | TP-122 | pen H S D A V F T D N Y T R L R K Q V A A K K Y L N W I K K G K R L L R K L Q P P P Z ste |

FIG. 2

| Sequence Identifier | Name | Amino Acid Sequence |
|---|---|---|
| SEQ ID NO: 39 | GLP1 | HAEGTFTSDVSSYLEGQAAKEFIAWLVKGR |
| SEQ ID NO: 40 | Exendin | HGEGTFTSDLSKQMEEEAVRLFIEWLKNGGPSSGAPPPS |
| SEQ ID NO: 41 | ZP-10 | HGEGTFTSDLSKQMEEEAVRLFIEWLKNGGPSSGAPPSKKKKKK |
| SEQ ID NO: 42 | PACAP frag | HSDGIFTDSYSRYRKQMAVKKYLAAVLGKRYKQRVKNK |
| SEQ ID NO: 43 | VIP | HSDAVFTDNYTRLRKQMAVKKYLNSILNGKRSSEGESP |
| SEQ ID NO: 44 | VPAC2 sel Bayer | HSDAVFTDNYTRLRKQVAAKKYLQSIKNKRY |
| SEQ ID NO: 45 | VPAC2 sel Bayer 2 | HSDAVFTDNYTRLRKQMAAKKYLNSIKNKR |
| SEQ ID NO: 46 | VPAC2 sel Bayer 3 | HSDAVFTDNYTRLRKQMAAKKYLNSIQNRR |
| SEQ ID NO: 47 | VPAC2 sel ULdB | hexHSDAVFTDNYTRLRKQMAAKKYLNSIKKGKRSSEGESP |
| SEQ ID NO: 48 | SQNM 11 | HSDAVFTDNYTRLRKQVAAKKYLQSIKQKRYELLEKLLRKLRTA |
| SEQ ID NO: 49 | SQNM 12 | HSDAVFTDNYTRLRKQVAAKKYLQSIKQKRELLEKLLRKLRTA |
| SEQ ID NO: 50 | SQNM 10 | HSDAVFTDNYTRLRKQVAAKKYLQSILGSRTSPPP |
| SEQ ID NO: 51 | GIP | YAEGTFISDYSIAMDKIHQQDFVNWLLAQKGKKNDWKHNTIQ |
| SEQ ID NO: 52 | Heliodermin | HSDAIFTQQYSKLLAKLALQKYLASILGSRTSPPP |

VASOACTIVE INTESTINAL POLYPEPTIDE PHARMACEUTICALS

FIELD OF THE INVENTION

The invention relates to polypeptide analogs and their synthesis and uses. More particularly, the invention relates to synthetic polypeptide analogs related to vasoactive intestinal polypeptide, and pharmaceutical compositions thereof.

BACKGROUND

When food is present in the alimentary canal, cells in the gut secrete a hormonal signal (an "incretin"), which sensitizes the pancreas to the presence of glucose and results in a potentiated glucose-dependent insulin secretory response. Such a synergistic response to provide glucose-dependent insulin release (Kieffer T J and Habener, J R (1999) Endocr. Rev. 20, 876-913) is seen for the incretin signals, Glucagon-like Peptide 1 (GLP1) and Glucose-dependent Insulinotropic Peptide (GIP). These incretin signals typically exhibit short duration of action in the body, with GLP1 exhibiting a t1/2 of approximately 1-2 minutes (Knudsen, L B 2004, J. Med. Chem. 47, 4128-34). GLP1 and GIP are cleaved by an amino peptidase, dipeptidyl peptidase IV (DPPIV) and thus, the naturally occurring native hormone is not generally used in medicinal formulations. A peptide found in the saliva of the Gila Monster (exendin 4, Exenatide; Amylin Pharmaceuticals, San Diego, Calif.) was shown to bind to the GLP1 receptor and exhibit potent agonistic activity, thereby imparting a desirable glucose-dependent insulin secretory response (Nielsen L L, Young, A A, Parkes, D G (2004) Regul. Peptides, 117, 77-88). Exenatide and analogs of GLP1 have been administered to patients in need of treatment for type 2 diabetes.

Pituitary Adenylate Cyclase-Activating Peptide (PACAP) is a neuromodulatory peptide which stimulates PAC1, VPAC1, and VPAC2 receptors, and is emitted from nerve endings in the pancreas. Receptors of this general class reside in multiple tissues in the body, including in the pancreas. In the pancreas, stimulation of the VPAC2 receptors have been shown to provide a potentiated, glucose-dependent insulin release in response to elevated blood glucose levels similar to that of GLP1 or exenatide (Tsutsumi, M., et al. (2002) Diabetes 51, 1453-60). Thus such a stimulus (from PACAP or VPAC agonistic analogs) could be synergistic or alternative to incretin-like signals in stimulating glucose-dependent insulin release, since a similar profile of potentiated insulin secretion results from activation of a second class of receptor. Such an effect would be beneficial in the treatment of metabolic disorders, including Type 2 Diabetes Mellitus (T2DM), metabolic acidosis, insulin resistance and obesity. However, the naturally occurring native sequence of PACAP and its analogs also are typically short-lived in the body.

Synthetic exendin-4 is a relatively short acting peptide and there is a medical need for longer-acting peptides that can modulate glucose-dependent insulin secretion.

SUMMARY OF THE INVENTION

The invention provides synthetic polypeptide analogs of PACAP and Vasoactive Intestinal Polypeptide (VIP), and salts thereof, in which the C-terminus comprises amino acid residues that form an amphipathic α-helix, said residues selected from hydrophilic amino acids (Haa) and lipophilic amino acids (Laa) ordered in the sequence:

Haa (Laa Laa Haa Haa)$_n$ Laa.

wherein n=1-5. In an embodiment, n=1 or 2.

Modifications introduced in the present polypeptide analogs of PACAP and VIP facilitate increased duration of action of therapeutics which activates the PACAP and VIP family of receptors, preferably the VPAC2 receptor. Without being bound to any particular theory, it is believed that an increase in duration of action may be due to the ability of the amphipathic helix in the C-terminal region to interact with the phospholipids of the cell membranes in the body and thereby have a "depoting" effect. Thus, the present peptide analogs are bound to cell membranes and then slowly re-released to the plasma to impart its effect distally. In contrast, if a peptide such as PACAP, VIP or GLP1 is free in the plasma it is rapidly acted upon by proteases or cleared by glomerular filtration.

Therefore, one aspect of the invention provides analogs to PACAP, VIP, and the physiologically active truncated analogs and homologs of same, or salts thereof, in which the C-terminus comprises amino acid residues that form an amphipathic α-helix, the sequence of said residues selected from the native amino acids or selected unnatural amino acids having the ability to stabilize said α-helix.

Also provided are pharmaceutical compositions for the delivery of an effective glucose-dependant insulin releasing amount of a polypeptide analog of PACAP, VIP, and the physiologically active truncated analogs and homologs of same, or a salt thereof, in which the C-terminus comprises amino acid residues that form an amphipathic α-helix, said residues selected from hydrophilic amino acids (Haa) and lipophilic amino acids (Laa) ordered in the sequence:

Haa (Laa Laa Haa Haa)$_n$ Laa;

wherein n=1-5.

The invention further provides methods for treating mammalian conditions characterized by high blood glucose, which methods comprise administering to a mammal in need thereof an effective glucose-dependant insulin releasing amount of a polypeptide analog of PACAP, VIP, and the physiologically active truncated analogs and homologs of same, or a salt thereof, in which the C-terminus comprises amino acid that form an amphipathic α-helix, said residues selected from hydrophilic amino acids (Haa) and lipophilic amino acids (Laa) ordered in the following sequence:

Haa (Laa Laa Haa Haa)$_n$ Laa;

wherein n=1-5.

The invention also includes processes for the solid phase synthesis of polypeptide analogs of PACAP, VIP, and the physiologically active truncated analogs and homologs of same, or a salt thereof, in which the C-terminus comprises amino acid residues that form an amphipathic α-helix, said residues selected from hydrophilic amino acids (Haa), and lipophilic amino acids (Laa) ordered in the following sequence:

Haa (Laa Laa Haa Haa)$_n$ Laa;

wherein n=1-5.

Processes presented herein for preparing polypeptide analogs comprise sequentially coupling protected amino acids on a suitable resin support, removing the side chain and Nα-protecting groups, and cleaving the polypeptide from the resin.

The invention also provides DNA sequences, vectors, and plasmids for the recombinant synthesis of polypeptide analogs of PACAP, VIP, and the physiologically active truncated analogs and homologs of same, or a salt thereof, in which the C-terminus comprises amino acid residues that form an amphipathic α-helix, said residues selected from hydrophilic amino acids (Haa) and lipophilic amino acids (Laa) ordered in the sequence:

Haa (Laa Laa Haa Haa)$_n$ Laa;

wherein n=1-5.

In addition, the invention provides pharmaceutical compositions and methods for the prevention and treatment of a variety of metabolic disorders, including diabetes, insulin resistance, hyperglycemia, metabolic acidosis and obesity, which are manifested by elevated blood glucose levels, comprising an effective amount of the polypeptide(s) of the invention, or salt thereof, and a pharmaceutically acceptable carrier. In other aspects of the invention, therapeutically effective amounts of metabolic disorder compounds, including insulin, insulin analogs, incretin, incretin analogs, glucagon-like peptide, glucagon-like peptide analogs, exendin, exendin analogs, sulfonylureas, biguanides, α-glucosidase inhibitors, thiazolidinediones, peroxisome proliferator activated receptor (PPAR) agonists, PPAR antagonists and PPAR partial agonists may be administered in combination with the polypeptides of the present invention.

BRIEF DESCRIPTION OF THE DRAWINGS

FIGS. 1A, 1B, and 1C are lists of exemplary polypeptide analogs according to the invention. Standard nomenclature using single letter abbreviations for amino acids are used. The letter "X" refers to a polyethylene glycol chain having $C_{10}$-$C_{3000}$ chain. The term "acyl" refers to a $C_2$-$C_{16}$ acyl chain. The letter "Z" refers to lysine having a long acyl chain at the epsilon position. The term "hex" refers to hexanoyl. The term "pen" refers to pentanoyl. The terms "lau" refers to lauroyl. The term "myr" refers to myristoyl. The term "ste" refers to stearoyl. The term "pr" refers to propionyl.

FIG. 2 lists other polypeptide and polypeptide analogs (SEQ ID NOs 39-52, respectively in order of appearance).

DETAILED DESCRIPTION OF THE INVENTION

Abbreviations and Definitions

The one- and three-letter abbreviations for the various common nucleotide bases and amino acids are as recommended in Pure Appl. Chem. 31, 639-645 (1972) and 40, 277-290 (1974) and comply with 37 CFR .sctn.1.822 (55 FR 18245, May 1, 1990). The abbreviations represent L-amino acids unless otherwise designated as D- or DL. Certain amino acids, both natural and non-natural, are achiral, e.g., glycine. All peptide sequences are presented with the N-terminal amino acid on the left and the C-terminal amino acid on the right.

"Hydrophilic amino acid (Haa)" refers to an amino acid having at least one hydrophilic functional group in addition to those required for peptide bond formation, such as arginine, asparagine, aspartic acid, glutamic acid, glutamine, histidine, lysine, serine, threonine, and their homologs.

"Lipophilic amino acid (Laa)" refers to an uncharged, aliphatic or aromatic amino acid, such as isoleucine, leucine, methionine, phenylalanine, tryptophan, tyrosine, valine, and their homologs.

In the invention, alanine is classified as "amphiphilic" i.e., capable of acting as either hydrophilic or lipophilic.

"Homolog of PACAP or VIP" refers to a polypeptide comprising amino acids in a sequence that is substantially similar to the native sequence of PACAP or VIP, such as at least 50, 60, 70, 80, 85, 90, 91, 92, 93, 94, 95, 96, 97, 98, or 99% amino acid sequence identity. Homologs presented herein may comprise amino acid substitutions, deletions, and/or insertions relative to the native sequence of PACAP or VIP. Exemplary homologs comprise a span of at least 5, 10, 15, 20, 25, 30, or 35 contiguous amino acids that is identical or substantially similar to the native sequence of PACAP or VIP.

"Analogs of PACAP or VIP" refers to a polypeptide comprising: (i) PACAP, VIP, and/or homologs of PACAP or VIP; and (ii) at least one functionality not present in naturally occurring native PACAP and/or VIP. For example, analogs can optionally comprise a functionality within the sidechain of an amino acid or at the amino or carboxyl terminal of the polypeptide. Exemplary functionalities include alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other exemplary functionalities that can be introduced include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto containing amino acids, amino acids comprising polyethylene glycol or polyether, heavy atom substituted amino acids, chemically cleavable and/or photocleavable amino acids, amino acids with an elongated side chains as compared to natural amino acids, e.g., polyethers or long chain hydrocarbons, e.g., greater than about 5 or greater than about 10 carbons, carbon-linked sugar-containing amino acids, redox-active amino acids, amino thioacid containing amino acids, and amino acids comprising one or more toxic moiety.

Analogs presented herein may comprise non-natural amino acids based on natural amino acids, such as tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, or the like. Glutamine analogs include, but are not limited to, α-hydroxy derivatives, β-substituted derivatives, cyclic derivatives, and amide substituted glutamine derivatives. Examples of phenylalanine analogs include, but are not limited to, meta-substituted phenylalanines, wherein the substituent comprises a hydroxy group, a methoxy group, a methyl group, an allyl group, an acetyl group, or the like. Specific examples include, but are not limited to, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAc.beta.-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like.

Generally, analogs are optionally designed or selected to modify the biological properties of the polypeptide, such as to modulate toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, redox potential, half-life, ability to react with other molecules, e.g., covalently or noncovalently, and the like.

"Physiologically active truncated homolog or analog of PACAP or VIP" refers to a polypeptide having a sequence comprising less than the full complement of amino acids found in PACAP or VIP which, however, elicits a similar physiological response. Representative truncated homologs and/or analogs presented herein comprise at least 5, 10, 15, 20, 25, 30, or 35 contiguous amino acids found in the native sequence of PACAP or VIP. The truncated PACAP or VIP need not be fully homologous with PACAP or VIP to elicit a similar physiological response. PACAP or VIP are preferred, but not exclusive, representatives of this group.

"PEG" refers to polyethylene glycol, polypropylene glycol, or polyoxyalkylenes. In an embodiment, PEG comprises a $C_{10}$-$C_{3000}$ chain. In another embodiment, PEG has a molecular weight above 40 kD. PEG is well known in the art and described, for example, in U.S. Pat. Nos. 4,640,835; 4,496,689; 4,301,144; 4,670,417; 4,791,192; and 4,179,337.

"Amphipathic α-helix" refers to the secondary structure exhibited by certain polypeptides in which the amino acids assume an α-helical configuration having opposing polar and nonpolar faces oriented along the long axis of the helix. The possibility of α-helical structure in the polypeptide of interest may be explored to some extent by the construction of a "Schiffer-Edmundson wheel" (M. Schiffer and A. B. Edmundson, Biophys. J. 7, 121 (1967), incorporated herein by reference), of the appropriate pitch and noting the segregation of the hydrophilic and lipophilic residues on opposite faces of the cylinder circumscribing the helix. Alternatively, empirical evidence, such as circular dichroism or x-ray diffraction data, may be available indicating the presence of an α-helical region in a given polypeptide. An ideal α-helix has 3.6 amino acid residues per turn with adjacent side chains separated by 100° of arc.

Polypeptides

In an embodiment, polypeptides presented herein comprise truncated portions of PACAP and/or VIP having at least 5, 10, 15, 20, 25, 30, or 35 contiguous amino acids of the native sequence of PACAP or VIP. In another embodiment, the present polypeptides share at least 50, 60, 70, 80, 85, 90, 95, or 99% amino acid sequence identity to the native sequence of PACAP or VIP. In yet another embodiment, the present polypeptides comprise a span of at least 5, 10, 15, 20, 25, 30, or 35 contiguous amino acids of PACAP and/or VIP having at least 50, 60, 70, 80, 85, 90, 91, 92, 93, 94, 95, 96, 97, 98, 99, or 100% amino acid sequence identity to the native sequence of PACAP or VIP.

Polypeptides presented herein optionally comprise modifications, functionalities, and/or amino acid substitutions which modulate VPAC2 selectivity. Exemplary modifications, functionalities, and/or substitutions include, but are not limited to, C-terminal cationic extensions and/or mutations reported in Gourlet et al. (Peptides 18, 403-8; Xia M, et al. (1997) and J. Pharmacol. Exp. Ther. 281: 629-33 (1997); the contents of both of which are incorporated herein by reference).

Modifications at the amino or carboxyl terminus may optionally be introduced into the present polypeptides. For example, the present polypeptides, such as analogs of VIP, can be acylated on the N-terminus by long chain fatty acids to yield polypeptides exhibiting low efficacy, partial agonist and antagonist activity (Gourlet et al., Eur. J. Pharmacol. 354: 105-111 (1998), the contents of which is incorporated herein by reference). Other exemplary modifications of the present polypeptides, such as analogs of VIP, include acylation with hexanoic acid to yield polypeptides that exhibit increased selectivity towards VPAC2 (Langer et al., Peptides 25: 275-8 (2004), the contents of which is incorporated herein by reference). Thus the length and positioning of such acylation can alter efficacy, and could result in loss of efficacy (antagonistic) or agonistic analogs. Contrary to this unpredictability, polypeptides presented herein have been designed and tested to obtain desired efficacy and activity.

Modifications may optionally be introduced within the side chain of at least one amino acid within the present polypeptides to increase duration of action and/or potency. For example, the present polypeptides can optionally comprise at least one amino acid acylated to a functionality in the side chain (i.e., R group). Representative modifications include fatty acid acylation of reactive side chains (such as Lys) at various positions within the polypeptide. Similar modifications have been reported in Kurtzhals et al. where acylation of insulin on LysB[29] resulted in insulin detemir (Kurtzhals et al., Biochem J. 312, 725-31 (1995), and Kurtzhals, P., Int. J. Obesity 28: Suppl 2, S23-8 (2004)). Similarly, acylation with long chain fatty acids through linker molecules has resulted in potent and long-acting analogs of GLP1 (Knudsen L B, et al. (2000). J. Med. Chem. 43, 1664-69), but the acylation can result in loss of activity or potent agonists, depending on the length and positioning of the acyl chain(s). Contrary to the unpredictable effects with the introduction of long chain fatty acids, polypeptides presented herein have been designed to incorporate an optimal number, length and positioning of the acyl chains so as to obtain desired activity.

Another type of modification that can optionally be introduced into the present polypeptides (e.g. within the polypeptide chain or at either the N- or C-terminal) to extend duration of action is PEGylation or incorporation of long-chain polyethylene glycol polymers (PEG). Introduction of PEG or long chain polymers of PEG increases the effective molecular weight of the present polypeptides to prevent rapid filtration into the urine. Methods for incorporating PEG or long chain polymers of PEG are well known in the art and described, for example, in Greenwald et al., Adv. Drug Del. Rev. 55: 217-250 (2003), the contents of which is incorporated herein by reference.

A more recently reported alternative approach for incorporating PEG or PEG polymers through incorporation of non-natural amino acids can be performed with the present polypeptides. This approach utilizes an evolved tRNA/tRNA synthetase pair and is coded in the expression plasmid by the amber suppressor codon (Deiters, A, et al. (2004). Bio-org. Med. Chem. Lett. 14, 5743-5). For example, p-azidophenylalanine can be incorporated into the present polypeptides and then reacted with a PEG polymer having an acetylene moiety in the presence of a reducing agent and copper ions to facilitate an organic reaction known as "Huisgen [3+2] cycloaddition".

Amphipathic Helix

Polypeptides of the present invention comprise amphipathic α-helix corresponding to the formula:

wherein n, Haa, and Laa are selected from the group of hydrophilic amino acids and the Laa's are selected from the group of lipophilic amino acids, as defined above. Without being bound to any particular theory, it is believed that the amphipathic helix in the C-terminal region imparts an increase in duration of action of the present polypeptides by interacting with the phospholipids of the cell membranes in the body and thereby have a "depoting" effect. Polypeptides of the present invention comprise a peptide region that is an amphipathic alpha helix, not merely an optimized alpha helix. Without wishing to be bound by any particular theory, the amphipathic alpha helix is believed to facilitate increased interaction with cell membranes and assist in proper placement of C-terminal fatty acyl chain modifications for membrane interaction.

Studies by Eisenberg et al. have combined a hydrophobicity scale with the helical wheel to quantify the concept of amphipathic helices (Nature 299: 371-374 (1982) and Proc. Nat. Acad. Sci. USA 81: 140-144 (1984); the disclosures of which are hereby incorporated by reference). The mean hydrophobic moment is defined as the vector sum of the hydrophobicities of the component amino acids making up the helix. The following hydrophobicities for the amino acids are those reported by Eisenberg et al. as the "consensus" scale: Ile 0.73; Phe 0.61; Val 0.54; Leu 0.53; Trp 0.37; Met 0.26 Ala 0.25; Gly 0.16; Cys 0.04; Tyr 0.02; Pro −0.07; Thr −0.18; Ser −0.26; His −0.40; Glu −0.62; Asn −0.64; Gln −0.69; Asp −0.72; Lys −1.10; Arg −1.76.

The hydrophobic moment, $\mu H$, for an ideal $\alpha$-helix having 3.6 residues per turn (or a 100° arc (=360°/3.6) between side chains), may be calculated from:

$$\mu H = [(\Sigma H_N \sin \delta(N-1))^2 + (\Sigma H_N \cos \delta(N-1))^2]^{1/2},$$

where $H_N$ is the hydrophobicity value of the $N^{th}$ amino acid and the sums are taken over the N amino acids in the sequence with periodicity $\delta=100°$. The hydrophobic moment may be expressed as the mean hydrophobic moment per residue by dividing $\mu H$ by N to obtain $<\mu H>$. A value of $<\mu H>$ at 100°+−0.20° of about 0.20 or greater is suggestive of amphipathic helix formation.

A study by Cornett et al. has further extended the study of amphipathic $\alpha$-helices by introducing the "amphipathic index" as a predictor of amphipathicity (J. Mol. Biol., 195: 659-685 (1987); the disclosure of which is hereby incorporated by reference). They concluded that approximately half of all known $\alpha$-helices are amphipathic, and that the dominant frequency is 97.5° rather than 100°, with the number of residues per turn being closer to 3.7 than 3.6. The basic approach of Eisenberg, et al. is sufficient to classify a given sequence as amphipathic, particularly when one is designing a sequence ab initio to form an amphipathic $\alpha$-helix.

A substitute amphipathic $\alpha$-helical amino acid sequence may lack homology with the sequence of a given segment of a naturally occurring polypeptide but elicits a similar secondary structure, i.e. an $\alpha$-helix having opposing polar and non-polar faces, in the physiological environment. Replacement of the naturally occurring amino acid sequence with an alternative sequence may beneficially affect the physiological activity, stability, or other properties of the altered parent polypeptide. Exemplary reports describing the design and selection of such sequences is provided in J. L. Krstenansky, et al., FEBS Letters 242: 2, 409-413 (1989), and J. P. Segrest, et al. Proteins: Structure, Function, and Genetics 8: 103-117 (1990) among others.

Polypeptides of the present invention comprise amphipathic $\alpha$-helix corresponding to the formula:

Haa (Laa Laa Haa Haa)$_n$ Laa wherein the Haa's are selected from the group of hydrophilic amino acids and the Laa's are selected from the group of lipophilic amino acids, as defined above. Assuming an idealized $\alpha$-helix in an embodiment where n=2, residues 1, 4, 5, 8, and 9 are distributed along one face (A) of the helix within about a 140° arc of each other, while residues 2, 3, 6, 7, and 10 occupy an opposing 140° arc on the other face (B) of the helix. In an embodiment, all the residues on one face are of the same polarity while all those on the other face are of the opposite polarity, i.e., if face A is all hydrophilic, face B is all lipophilic and vice versa. The skilled artisan will recognize that while the helices of the invention are described by Haa(Laa Laa Haa Haa)$_n$ Laa, the reverse sequence, Laa (Haa Haa Laa Laa)$_n$ Haa will also meet the residue distribution criteria and is an equivalent descriptor of the helices of the invention.

Alanine may be substituted for either hydrophilic or lipophilic amino acids, since Ala can reside readily on either face of an amphipathic $\alpha$-helix, although Ala-10 does not form an amphipathic $\alpha$-helix. Generally, proline, cysteine, and tyrosine are not used; however, their presence and other random errors in the sequence may be tolerated, e.g. a hydrophilic residue on the lipophilic face, as long as the remaining amino acids in the segment substantially conform to the hydrophilic face—lipophilic face division. A convenient method for determining if a sequence is sufficiently amphipathic to be a sequence of this invention is to calculate the mean hydrophobic moment, as defined above. If the peak mean moment per residue at 100°+−20° exceeds about 0.20, then the sequence will form an amphipathic helix and is a sequence of the invention.

In applying this concept to PACAP and VIP, it is hypothesized that either or both regions (N-terminal or C-terminal), preferably the C-terminal, may exhibit $\alpha$-helical secondary structure and could be replaced with a non-homologous sequence having similar structural tendencies, without loss of biological activity or induction of immunoreaction.

Pharmaceutical Formulations

Polypeptides of the present invention may be administered in any amount to impart beneficial therapeutic effect. In a preferred embodiment, compounds of the present invention are useful in the treatment of elevated blood glucose levels, hyperglycemia, diabetes, including Type 2 Diabetes Mellitus, insulin resistance, metabolic acidosis and obesity. In an embodiment, compounds presented herein impart beneficial activity in the modulation of insulin and/or glucose levels. In an embodiment, the present polypeptides are administered to a patient at concentrations higher or lower than that of other forms of treatment which modulate insulin and/or glucose secretion. In yet another embodiment, the present polypeptides are administered with other compounds to produce a synergistic therapeutic effect. For example, polypeptides of the invention may be administered in conjunction with exendin or exendin analogs.

EXAMPLES

Example 1

Synthetic Analogs

Some of the exemplary synthetic polypeptide analogs illustrated in FIG. 1 are derived from VPAC2 sel UldB (see FIG. 1). Other exemplary synthetic polypeptide analogs illustrated in FIG. 1 are truncated homologs of VIP (see FIG. 1).

In one aspect, the present polypeptide analogs of the physiologically active truncated homologs of VIP, such as those shown in FIG. 1 as TP 1 to TP 6. Analogs TP 1 to TP 6 have a long acyl residue comprising $C_{12}$-$C_{24}$, preferably $C_{16}$-$C_{24}$. Analogs TP 7 to TP 12 shown in FIG. 1 have an acyl residue on the N-terminus comprising $C_2$-$C_{16}$, preferably $C_6$. Analogs SQNM 10-12 (corresponding to SEQ ID NO: 48-50) shown in FIG. 2 do not contain acylation at either the C or N-termini.

Other representative polypeptide analogs presented herein have amino acid sequences corresponding to general formula (I) (SEQ ID NOs: 53-55):

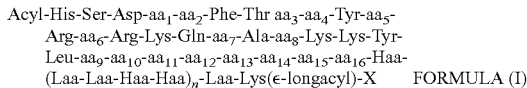

FORMULA (I)

wherein:
n=1-3;
Haa is a hydrophilic amino acid;
Laa is a lipophilic amino acid;
acyl is a $C_{2-16}$ acyl chain;
long acyl is a $C_{12-24}$ acyl chain;
X is OH or NHR1 where R1 is H or lower alkyl, haloalkyl, or PEG;
$aa_1$ is Gly or Ala;
$aa_2$ is Val, Ile, or Leu;
$aa_3$ is Asp or Arg;
$aa_4$ is Ser or Asn;
$aa_5$ is Ser or Thr;
$aa_6$ is Leu or Tyr;
$aa_7$ is Met, Leu, or Val;
$aa_8$ is Ala or Val;
$aa_9$ is Asn, Gln, or Ala;
$aa_{10}$ is Trp, Ala, or Ser;
$aa_{11}$ is Ile or Val;
$aa_{12}$ is Leu or Lys;
$aa_{13}$ is Lys, Arg, Asn, or Gly;
$aa_{14}$ is Ala or Gly;
$aa_{15}$ is Lys or Arg; and
$aa_{16}$ is Lys or Arg.

In a preferred embodiment, acyl is a $C_{2-8}$ acyl chain and long acyl is a $C_{12-24}$ acyl chain.

Other representative polypeptide analogs presented herein have amino acid sequences corresponding to general formula (II) (SEQ ID NOs: 56-61):

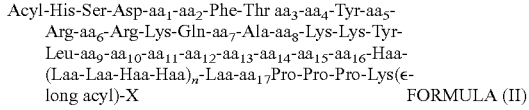

FORMULA (II)

wherein:
n=1-3;
Haa is a hydrophilic amino acid;
Laa is a lipophilic amino acid;
acyl is a $C_{2-16}$ acyl chain;
long acyl is a $C_{12-24}$ acyl chain;
X is OH or NHR1 where R1 is H or lower alkyl, haloalkyl, or PEG;
$aa_1$ is Gly or Ala;
$aa_2$ is Val, Ile, or Leu;
$aa_3$ is Asp or Arg;
$aa_4$ is Ser or Asn;
$aa_5$ is Ser or Thr;
$aa_6$ is Leu or Tyr;
$aa_7$ is Met, Leu, or Val;
$aa_8$ is Ala or Val;
$aa_9$ is Asn, Gln, or Ala;
$aa_{10}$ is Trp, Ala, or Ser;
$aa_{11}$ is Ile or Val;
$aa_{12}$ is Leu or Lys;
$aa_{13}$ is Lys, Arg, Asn, or Gly;
$aa_{14}$ is Ala or Gly;
$aa_{15}$ is Lys or Arg;
$aa_{16}$ is Lys or Arg; and
$aa_{17}$ is absent or Gln.

In a preferred embodiment, acyl is a $C_{2-8}$ acyl chain and long acyl is a $C_{12-24}$ acyl chain.

Other representative polypeptide analogs presented herein have amino acid sequences corresponding to general formula (III) (SEQ ID NOs: 62-64):

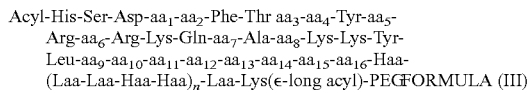

FORMULA (III)

wherein:
n=1-3;
Haa is a hydrophilic amino acid;
Laa is a lipophilic amino acid;
acyl is a $C_{2-16}$ acyl chain;
long acyl is a $C_{12-24}$ acyl chain;
$aa_1$ is Gly or Ala;
$aa_2$ is Val, Ile, or Leu;
$aa_3$ is Asp or Arg;
$aa_4$ is Ser or Asn;
$aa_5$ is Ser or Thr;
$aa_6$ is Leu or Tyr;
$aa_7$ is Met, Leu, or Val;
$aa_8$ is Ala or Val;
$aa_9$ is Asn, Gln, or Ala;
$aa_{10}$ is Trp, Ala, or Ser;
$aa_{11}$ is Ile or Val;
$aa_{12}$ is Leu or Lys;
$aa_{13}$ is Lys, Arg, Asn, or Gly;
$aa_{14}$ is Ala or Gly;
$aa_{15}$ is Lys or Arg; and
$aa_{16}$ is Lys or Arg.

In a preferred embodiment, acyl is a $C_{2-8}$ acyl chain and long acyl is a $C_{12-24}$ acyl chain.

The skilled artisan will appreciate that numerous permutations of the polypeptide analogs may be synthesized which will possess the desirable attributes of those described herein provided that an amino acid sequence having a mean hydrophobic moment per residue at 100°+−20° greater than about 0.20 is inserted at positions in the C-terminal region.

Example 2

General Method for Synthesizing Polypeptides

The polypeptides of the invention may be synthesized by methods such as those set forth in J. M. Stewart and J. D. Young, Solid Phase Peptide Synthesis, 2nd ed., Pierce Chemical Co., Rockford, Ill. (1984) and J. Meienhofer, Hormonal Proteins and Peptides, Vol. 2, Academic Press, New York, (1973) for solid phase synthesis and E. Schroder and K. Lubke, The Peptides, Vol. 1, Academic Press, New York, (1965) for solution synthesis and Houben-Weyl, *Synthesis of Peptides and Peptidomimetics*. 4th ed. Vol E22; M. Goodman, A. Felix, L. Moroder, C. Toniolo, Eds., Thieme: New York, 2004 for general synthesis techniques. The disclosures of the foregoing treatises are incorporated by reference herein.

In general, these methods involve the sequential addition of protected amino acids to a growing peptide chain. Normally, either the amino or carboxyl group of the first amino acid and any reactive side chain group are protected. This protected amino acid is then either attached to an inert solid support, or utilized in solution, and the next amino acid in the sequence, also suitably protected, is added under conditions amenable to formation of the amide linkage. After all the desired amino acids have been linked in the proper sequence, protecting groups and any solid support are removed to afford the crude polypeptide. The polypeptide is desalted and purified, preferably chromatographically, to yield the final product.

A preferred method of preparing the analogs of the physiologically active truncated polypeptides, having fewer than about forty amino acids, involves solid phase peptide synthesis. In this method the α-amino (Nα) functions and any reactive side chains are protected by acid- or base-sensitive groups. The protecting group should be stable to the conditions of peptide linkage formation, while being readily removable without affecting the extant polypeptide chain. Suitable α-amino protecting groups include, but are not limited to t-butoxycarbonyl (Boc), benzyloxycarbonyl (Cbz), o-chlorobenzyloxycarbonyl, biphenylisopropyloxycarbonyl, t-amyloxycarbonyl (Amoc), isobornyloxycarbonyl, α, α-dimethyl-3,5-dimethoxybenzyloxy-carbonyl, o-nitrophenylsulfenyl, 2-cyano-t-butoxycarbonyl, 9-fluorenyl-methoxycarbonyl (Fmoc) and the like, preferably t-butoxycarbonyl (Boc). Suitable side chain protecting groups include, but are not limited to: acetyl, benzyl (Bzl), benzyloxymethyl (Bom), o-bromobenzyloxycarbonyl, t-butyl, t-butyldimethylsilyl, 2-chlorobenzyl (Cl-z), 2,6-dichlorobenzyl, cyclohexyl, cyclopentyl, isopropyl, pivalyl, tetrahydropyran-2-yl, tosyl (Tos), trimethylsilyl, and trityl.

In solid phase synthesis, the C-terminal amino acid is first attached to a suitable resin support. Suitable resin supports are those materials which are inert to the reagents and reaction conditions of the stepwise condensation and deprotection reactions, as well as being insoluble in the media used. Examples of commercially available resins include styrene/divinylbenzene resins modified with a reactive group, e.g., chloromethylated co-poly-(styrene-divinylbenzene), hydroxymethylated co-poly-(styrene-divinylbenzene), and the like. Benzylated, hydroxymethylated phenylacetamidomethyl (PAM) resin is preferred. When the C-terminus of the compound is an amide, a preferred resin is p-methylbenzhydrylamino-co-poly(styrene-divinyl-benzene) resin.

Attachment to the PAM resin may be accomplished by reaction of the Nα protected amino acid, preferably the Boc-amino acid, as its ammonium, cesium, triethylammonium, 1,5-diazabicyclo-[5.4.0]undec-5-ene, tetramethylammonium, or similar salt in ethanol, acetonitrile, N,N-dimethylformamide (DMF), and the like, preferably the cesium salt in DMF, with the resin at an elevated temperature, for example between about 40° and 60° C., preferably about 50° C., for from about 12 to 72 hours, preferably about 48 hours.

The Nα-Boc-amino acid may be attached to the benzhydrylamine resin by means of, for example, an N,N'-diisopropylcarbodiimide (DIC)/1-hydroxybenzotriazole (HOBt) mediated coupling for from about 2 to about 24 hours, preferably about 2 hours at a temperature of between about 10° and 50° C., preferably 25° C. in a solvent such as dichloromethane or dimethylformamide, preferably dichloromethane.

The successive coupling of protected amino acids may be carried out by methods well known in the art, typically in an automated peptide synthesizer. Following neutralization with triethylamine or similar base, each protected amino acid is preferably introduced in approximately 1.5 to 2.5 fold molar excess and the coupling carried out in an inert, nonaqueous, polar solvent such as dichloromethane, DMF, or mixtures thereof, preferably in dichloromethane at ambient temperature. Representative coupling agents are N,N'-dicyclohexylcarbodiimide (DCC), N,N'-diisopropyl-carbodiimide (DIC) or other carbodiimide, either alone or in the presence of 1-hydroxybenzotriazole (HOBt), O-acyl ureas, benzotriazol-1-yl-oxytris(pyrrolidino)phosphonium hexafluorophosphate (PyBop), N-hydroxysuccinimide, other N-hydroxyimides, or oximes. Alternatively, protected amino acid active esters (e.g. p-nitrophenyl, pentafluorophenyl and the like) or symmetrical anhydrides may be used.

At the end of the solid phase synthesis the fully protected peptide is removed from the resin. When the linkage to the resin support is of the benzyl ester type, cleavage may be effected by means of aminolysis with an alkylamine or fluoroalkylamine for peptides with an alkylamide C-terminus, or by aminolysis with, for example, ammonia/methanol or ammonia/ethanol for peptides with an unsubstituted amide C-terminus, at a temperature between about −10° and 50° C., preferably about 25° C., for between about 12 and 24 hours, preferably about 18 hours. Peptides with a hydroxy C-terminus may be cleaved by HF or other strongly acidic deprotection regimen or by saponification. Alternatively, the peptide may be removed from the resin by transesterification, e.g., with methanol, followed by aminolysis or saponification. The protected peptide may be purified by silica gel chromatography.

The side chain protecting groups may be removed from the peptide by treating the aminolysis product with, for example, anhydrous liquid hydrogen fluoride in the presence of anisole or other carbonium ion scavenger, treatment with hydrogen fluoride/pyridine complex, treatment with tris(trifluoroacetyl)boron and trifluoroacetic acid, by reduction with hydrogen and palladium on carbon or polyvinylpyrrolidone, or by reduction with sodium in liquid ammonia, preferably with liquid hydrogen fluoride and anisole at a temperature between about −10° and +10° C., preferably at about 0° C., for between about 15 minutes and 2 hours, preferably about 1.5 hours.

For peptides on the benzhydrylamine resin, the resin cleavage and deprotection steps may be combined in a single step utilizing liquid hydrogen fluoride and anisole as described above.

The solution may be desalted (e.g. with BioRad AG-3.RTM. anion exchange resin) and the peptide purified by a sequence of chromatographic steps employing any or all of the following types: ion exchange on a weakly basic resin in the acetate form; hydrophobic adsorption chromatography on underivatized co-poly(styrene-divinylbenzene), e.g. Amberlite.RTM. XAD; silica gel adsorption chromatography; ion exchange chromatography on carboxymethylcellulose; partition chromatography, e.g. on Sephadex.RTM. G-25; counter-current distribution; or high performance liquid chromatography (HPLC), especially reversed-phase HPLC on octyl- or octadecylsilylsilica (ODS) bonded phase column packing.

Thus, another aspect of the present invention relates to processes for preparing polypeptides and pharmaceutically acceptable salts thereof, which processes comprise sequentially condensing protected amino acids on a suitable resin support, removing the protecting groups and resin support, and purifying the product, to afford analogs of the physiologically active truncated homologs and analogs of PACAP and VIP, preferably of PACAP and VIP in which the amino acids at the C-terminus form an amphipathic α-helical peptide sequence, as defined above.

Example 3

Exemplary Synthesis and Purification Protocol for a Representative Polypeptide Analog Representative polypeptide analog corresponding to SEQ ID NO: 1 was prepared using the synthetic and purification methods described below.

Pentanoyl-His-Ser-Asp-Ala-Val-Phe-Thr-Asp-Asn-
Tyr-Thr-Arg-Leu-Arg-Lys-Gln-Val-Ala-Ala-Lys-
Lys-Tyr-Leu-Asn-Trp-Ile-Lys-Lys-Ala-Lys-Arg-
Glu-Leu-Leu-Glu-Lys-Leu-Lys(epsilon stearoyl)-
NH$_2$ (SEQ ID NO: 1)

Generally, the peptide was synthesized on Fmoc-Rink-Amide-PEG resin via Fmoc chemistry. Protecting groups used for amino acid side chain functional groups are: t-Butyl group for Glu, Tyr, Thr, Asp and Ser; Boc group for Lys and Trp; Pbf group for Arg; Trt group for Asn and His. N-alpha Fmoc protected amino acids were purchased from EMD Biosciences (San Diego, Calif.). Reagents for coupling and cleavage were purchased from Aldrich (St. Louis, Mo.). Solvents were purchased from Fisher Scientific (Fairlawn, N.J.).

Generally, the synthetic protocol involved assembly of the peptide chain on resin by repetitive removal of the Fmoc protecting group and coupling of protected amino acid. For the synthesis, Dde-Lys(Fmoc)-OH was coupled onto the Rink Amide resin first. The Fmoc protecting group was then removed by 20% piperidine in DMF. Stearic acid was coupled onto the side chain of Lys using HBTU, HOBt and NMM. The Dde group was removed by 2% hydrazine in DMF and the next Fmoc protected amino acid was coupled. HBTU and HOBt were used as coupling reagent and NMM was used as base. After removal of last Fmoc protecting group, valeric acid (4 equivalents) was coupled to the amino terminus with DIC (4 equivalents) and HOBt (4 equivalents). The peptide resin was treated with cocktail 1 for cleavage and removal of the side chain protecting groups. Crude peptide was precipitated from cold ether and collected by filtration.

Purification of crude peptide was achieved via RP-HPLC using 20 mm×250 mm column from Waters (Milford, Mass.). Peptide was purified using TFA Buffer. A linear gradient of 35% to 55% acetonitrile in 60 minutes was used. Pooled fractions were lyophilized. The peptide identity was verified by mass spectrometry analysis and amino acid analysis. The peptide purity was determined by analytical HPLC column (C18 column, 4.6×250 mm, manufactured by Supelco (St. Louis, Mo.)) chromatography.

The above procedure can be summarized in the following step wise protocol:

Step 1. Resin swelling: Fmoc-Rink-Amide-PEG resin was swelled in DCM for 30 minutes (10 ml/g resin)

Step 2. Deprotection:
  a. 20% piperidine/DMF solution (10 ml/g resin) was added to the resin;
  b. Solution stirred for 30 minutes (timing was started when all the resin was free floating in the reaction vessel); and
  c. Solution was drained.

Step 3. Washing: Resin was washed with DMF (10 ml/g resin) five times. The ninhydrin test was performed and appeared positive.

Step 4. Coupling:
  a. Fmoc-AA-OH (3 equivalents calculated relative to resin loading) and HOBt (3 equivalents relative to resin loading) was weighed into a plastic bottle.
  b. Solids were dissolved with DMF (5 ml/g resin).
  c. HBTU (3 equivalents relative to resin loading) was added to the mixture, followed by the addition of NMM (6 equivalents relative to resin loading).
  d. Mixture was added to the resin.
  e. Mixture was bubbled (or stirred) gently for 10-60 minutes until a negative ninhydrin test on a small sample of resin was obtained.

Step 5. Washing: Resin was washed three times with DMF.

Step 6. Steps 2-5 were repeated until the peptide was assembled.

Step 7. N-terminal Fmoc Deprotection: Step 2 was repeated.

Step 8. Washing and Drying:
  a. After the final coupling, resin was washed three times with DMF, one time with MeOH, three times with DCM, and three times with MeOH.
  b. Resin was dried under vacuum (e.g., water aspirator) for 2 hours and high vacuum (oil pump) for a minimum of 12 hours.

Step 9. Cleavage:
  a. Dry resin was placed in a plastic bottle and the cleavage cocktail was added. The mixture was shaken at room temperature for 2.5 hours.
  b. The resin was removed by filtration under reduced pressure. The resin was washed twice with TFA. Filtrates were combined and an 8-10 fold volume of cold ether was added to obtain a precipitate.
  c. Crude peptides were isolated by filtration and then washed twice with cold ether.

The following chemicals and solvents were used in the synthetic protocol described above: NMM (N-Methylmorpholine); HBTU (2-(1H-Benzotriazole-1-yl)-1,1,3,3-tetramethyluronium Hexafluorophosphate); HOBt (1-Hydroxybenzotriazole); DMF (Dimethylformamide); DCM (Dichloromethane); Methanol; Diethylether; Piperidine; Tis (Triisopropylsilane); Thioanisole; Phenol; EDT (1,2-Ethanedithiol); Trifluoroacetic acid Cocktail 1: TFA/Thioanisole/Phenol/ H$_2$O/EDT (87.5/5/2.5/2.5/2.5 v/v/); TFA buffer: A (0.1% TFA in water); and TFA buffer B (0.1% TFA in Acetonitrile).

Other representative polypeptide analogs were prepared in a manner similar to that described above. Listed below in TABLE 1 are chemical properties of exemplary polypeptide analogs of the invention.

TABLE 1

Properties of Exemplary Polypeptide Analogs

| Name of Analog | Amino Acid Sequence | Purity Based on RP-HPLC Chromatogram | Molecular Weight Based on Electrospray Mass Spectrometry |
|---|---|---|---|
| TP-103 | SEQ ID NO: 2 | 96.9% | 5267.2 a.m.u. |
| TP-104 | SEQ ID NO: 3 | 95.5% | 4756.7 a.m.u. |
| TP-105 | SEQ ID NO: 4 | 96.1% | 5183.3 a.m.u. |
| TP-106 | SEQ ID NO: 5 | 95.2% | 4784.8 a.m.u. |
| TP-107 | SEQ ID NO: 6 | 99.6% | 4955.1 a.m.u. |
| TP-108 | SEQ ID NO: 7 | 91.5% | 5172.4 a.m.u. |

Example 4

Recombinant Synthesis of the Polypeptides

Alternatively, the polypeptides of the present invention may be prepared by cloning and expression of a gene encoding for the desired polypeptide. In this process, a plasmid containing the desired DNA sequence is prepared and inserted into an appropriate host microorganism, typically a bacteria, such as E. coli, or a yeast, such as Saccharomyces cerevisiae, inducing the host microorganism to produce multiple copies of the plasmid, and so of the cDNA encoding for the polypeptide analogs of the invention.

First, a synthetic gene coding for the selected PACAP or VIP analog is designed with convenient restriction enzyme cleavage sites to facilitate subsequent alterations. Polymerase chain reaction (PCR), as taught by Mullis in U.S. Pat. Nos. 4,683,195 and 4,683,202, incorporated herein by reference, may be used to amplify the sequence.

The amplified synthetic gene may be isolated and ligated to a suitable plasmid, such as a Trp LE plasmid, into which four copies of the gene may be inserted in tandem. Preparation of Trp LE plasmids is described in U.S. Pat. No. 4,738,921 and European Patent Publication No. 0212532, incorporated herein by reference. Trp LE plasmids generally produce 8-10 times more protein than Trp E plasmids. The multi-copy gene may then be expressed in an appropriate host, such as E. coli or S. cerevisiae.

Trp LE 18 Prot (Ile$^3$, Pro$^5$) may be used as an expression vector in the present invention. Trp LE 18 Prot (Ile$^3$, Pro$^5$) contains the following elements: a pBR322 fragment (EcoRI-BamHI) containing the ampicillin resistant gene and the plasmid origin of replication; an EcoRI-SacII fragment containing the trp promoter and the trpE gene; an HIV protease (Ile$^3$, Pro$^5$) gene fragment (SacII-HindIII); a bGRF gene fragment (HindIII-BamHI); and a transcription terminator from E. coli rpoc gene. The HIV protease and bGRF gene fragments are not critical and may be replaced with other coding sequences, if desired.

The expressed multimeric fusion proteins then accumulate intracellularly into stable inclusion bodies and may be separated by centrifugation from the rest of the cellular protein. The isolated fusion protein is converted to the monomeric PACAP or VIP analog and may be purified by cation exchange and/or reverse phase HPLC.

Alternative methods of cloning, amplification, expression, and purification will be apparent to the skilled artisan. Representative methods are disclosed in Maniatis, et al., Molecular Cloning, a Laboratory Manual, 3rd Ed., Cold Spring Harbor Laboratory (2001), incorporated herein by reference.

Example 5

In Vitro Bioassay with Islet Cell Static Cultures

The following exemplary in vitro bioassay was conducted to evaluate the ability of representative polypeptide analogs to modulate insulin secretion.

Islet isolation. Rat islets were harvested (Sweet I R, et al. (2004) Biochem. Biophys. Res. Commun. 314, 976-983) from male Fisher rats weighing about 250 g and which were anesthetized by intraperitoneal injection of sodium pentobarbital (35 mg/230 g rat). Generally, the islets were prepared by injecting collagenase (10 mL of 0.23 mg/mL Liberase, Roche Molecular Biochemicals, Indianapolis, Ind.) into the pancreatic duct of the partially dissected pancreas and surgically removing it. All procedures were approved by the Institutional Animal Care and Use Committee at the University of Washington.

The pancreata were placed into 15 mL conical tubes containing 5 mL of 0.23 mg/mL Liberase and incubated at 37° C. for 30 min. The digestate was then filtered through a 400-micrometer stainless steel screen, rinsed with Hanks' buffered salt solution, and purified in a gradient solution of Optiprep (Nycomed, Oslo, Norway). Islets were cultured for 18-24 h prior to performing the assay in RPMI Media 1640 supplemented with 10% (v/v) heat inactivated fetal bovine serum (FBS), antibiotic-antimycotic (100 U/mL penicillin, 100 lg/mL streptomycin, and 0.25 lg/mL amphotericin B), 2 mM glutamine (all from Gibco-BRL, Grand Island, N.Y.), and 1 mM beta mercaptoethanol.

Bioassay. Islets were picked under a microscope and placed into 10 ml 3 mM Krebs Ringer Buffer (KRB) solution for washing. Islets were incubated in 3 mM glucose KRB for 60 min and then groups of 10 islets per well were placed into 200 μl media in a 96-well plate. The islets were incubated for 120 min under control or treatment conditions, and supernatants were collected. A typical set of conditions tested 3 mM glucose (resting control), 16 mM glucose (testing control), 16 mM glucose+10 nm GLP1, 16 mM glucose+10 nM Exendin-4, 16 mM glucose+50 nM test peptide. The buffer conditions were KRB with 0.1% BSA, 20 mM HEPES and the assay was performed in quadruplicate. Supernatants were evaluated for insulin content using a commercial insulin enzyme-linked immunosorbent (ELISA) assay per manufacturer's directions.

Results of Bioassay. TABLE 2 illustrates the insulin secretion obtained in the above assay for analog TP-106, which exhibited maximal activity in this assay at a concentration of 200 nM. For comparison, Exendin 4 was tested in this assay and showed maximal activity at 10 nM. TP-106 is a highly hydrophobic analog, designed to depot in the site of sc injection and therefore the effective concentration of TP-106 is expected to be much lower than the nominal concentration (200 nM).

TABLE 2

Results of Islet Cell Static Culture Bioassay with TP-106

|  | Insulin secreted (ng/100 islets/min) | Standard Deviation |
|---|---|---|
| 3 mM glucose | 0.01 | 0.00 |
| 16 mM glucose | 1.38 | 0.17 |
| Exendin 4 + 16 mM glucose | 4.82 | 0.20 |
| 50 nM TP-106 + 16 mM glucose | 2.72 | 0.60 |
| 200 nM TP-106 + 16 mM glucose | 5.20 | 0.50 |
| 16 mM glucose + 16 mM glucose | 1.58 | 0.05 |

The islet cell static culture assay described above was performed on additional exemplary polypeptide analogs. TP-107 exhibited maximal activity in this assay at a concentration of 100 nM. For comparison, Exendin 4 was tested in this assay and showed maximal activity at 10 nM. Presented peptides were designed to bind to serum albumin and thus, the concentration of free peptide to impart insulin activity is expected to be much lower and therefore the analog more potent than indicated in this in vitro assay.

TABLE 3

Results of Islet Cell Static Culture Bioassay with TP-107 and TP-108

|  | Average Insulin secreted (ng/100 islets/min) | Standard Deviation |
|---|---|---|
| 3 mM glucose | 0.14 | 0.00 |
| 16 mM glucose | 3.65 | 0.80 |
| 10 nM Exendin 4 + 16 mM glucose | 6.75 | 1.15 |

TABLE 3-continued

Results of Islet Cell Static Culture Bioassay with TP-107 and TP-108

|  | Average Insulin secreted (ng/100 islets/min) | Standard Deviation |
|---|---|---|
| 10 nM PACAP + 16 mM glucose | 6.07 | 1.67 |
| 10 nM TP-107 + 16 mM glucose | 2.89 | 0.21 |
| 100 nM TP-107 + 16 mM glucose | 6.10 | 1.55 |
| 1 uM TP-107 + 16 mM glucose | 6.07 | 0.90 |
| 100 nM TP-108 + 16 mM glucose | 4.10 | 1.21 |
| 1 uM TP-108 + 16 mM glucose | 5.65 | 0.13 |

Example 6

In Vivo Bioassay

The following exemplary in vivo assay was conducted to evaluate the ability of representative polypeptide analogs to modulate insulin secretion.

Tested Study Groups. Naïve, 8 weeks old female db/db mice were acclimated for one week, during which period animals were handled periodically to allow them to be acclimated to experiment procedures. Study groups contained 6 mice per group and were administered with one of the following by intraperitoneal injection:

(1) Vehicle control;
(2) Positive control (exendin-4 or other standard treatment);
(3) Polypeptide Analog at high dose; or
(4) Polypeptide Analog at low dose.

A small volume of blood was taken from a cut at the tip of tail for blood sampling. Blood glucose levels were determined on a commercial, hand-held glucose meter. On Day 1, animals were injected with polypeptide analogs and controls in the morning. Blood samples were taken and analyzed immediately before injection and at 2, 4, 8, 14, and 24 hours after injection. Animals were allowed to feed, ad libitum, throughout the assay (Tsutsumi et al., Diabetes 51:1453-60 (2002)).

TABLE 4 lists a representative sampling of the data obtained from the in vivo assay described above. As shown below, TP-106 exhibited statistically significant activity (e.g., reduced plasma glucose) at a high dose 2 hr after injection and maintains activity at 4 hrs post dosing.

TABLE 4

Results of In Vivo Assay with TP-103 and TP-106 Mean Blood Glucose Levels (mmol/L)

|  | 0 hr | 2 hr | 4 hr | 8 hr | 14 hr | 24 hr |
|---|---|---|---|---|---|---|
| Vehicle | 23.9<br>s.d.* = 1.33 | 21.9<br>s.d. = 1.22 | 18.3<br>s.d. = 1.01 | 27.3<br>s.d. = 1.52 | 22.5<br>s.d. = 1.25 | 23.5<br>s.d. = 1.31 |
| TP-103 Low dose | 22.9<br>s.d. = 1.27 | 20.5<br>s.d. = 1.14 | 17.6<br>s.d. = 0.98 | 26.4<br>s.d. = 1.47 | 24.6<br>s.d. = 1.37 | 21.4<br>s.d. = 1.19 |
| TP-103 High dose | 20.7<br>s.d. = 1.15 | 17.3<br>s.d. = 0.96 | 16.9<br>s.d. = 0.94 | 23.4<br>s.d. = 1.30 | 23.7<br>s.d. = 1.31 | 25.0<br>s.d. = 1.39 |
| TP-106 Low dose | 23.9<br>s.d. = 1.33 | 20.5<br>s.d. = 1.14 | 16.1<br>s.d. = 0.89 | 24.0<br>s.d. = 1.33 | 28.2<br>s.d. = 1.57 | 23.2<br>s.d. = 1.29 |
| TP-106 High dose | 21.8<br>s.d. = 1.21 | 13.4<br>s.d. = 0.75 | 14.7<br>s.d. = 0.82 | 25.1<br>s.d. = 1.39 | 26.3<br>s.d. = 1.46 | 21.2<br>s.d. = 1.18 |

*s.d. = standard deviation

Example 7

Uses of the Invention

The polypeptides of the present invention are useful for the prevention and treatment of a variety of metabolic disorders. In particular, the compounds of the present invention are indicated for the prophylaxis and therapeutic treatment of elevated blood glucose levels, hyperglycemia, diabetes, including Type 2 Diabetes Mellitus, insulin resistance, metabolic acidosis and obesity.

In general, the polypeptides of the invention, or salts thereof, are administered in amounts between about 0.01 and 1 µg/kg body weight per day, preferably from about 0.07 to about 0.2 µg/kg body weight per day. For a 50 kg human female subject, the daily dose of active ingredient is from about 0.5 to about 50 µg, preferably from about 3.5 to about 10 µg. In other mammals, such as horses, dogs, and cattle, higher doses may be required. This dosage may be delivered in a conventional pharmaceutical composition by a single administration, by multiple applications, or via controlled release, as needed to achieve the most effective results, preferably one or more times daily by injection.

In another embodiment, the polypeptides of the invention may be administered in combination with other compounds useful in the treatment of metabolic disorders. For example, the polypeptides of the invention may be administered with one or more of the following compounds used in the treatment of metabolic disorders, including but not limited to insulin, insulin analogs, incretin, incretin analogs, glucagon-like peptide, glucagon-like peptide analogs, exendin, exendin analogs, sulfonylureas, biguanides, α-glucosidase inhibitors, thiazolidinediones, peroxisome proliferator activated receptor (PPAR, of which includes agents acting on the α, β, or γ subtypes of PPAR receptors and/or those agent acting on multiple subtypes of the PPAR receptors) agonists, PPAR antagonists and PPAR partial agonists may be administered in combination with the polypeptides of the present invention.

The selection of the exact dose and composition and the most appropriate delivery regimen will be influenced by, inter alia, the pharmacological properties of the selected polypeptide, the nature and severity of the condition being treated, and the physical condition and mental acuity of the recipient.

Representative delivery regimens include oral, parenteral (including subcutaneous, intramuscular and intravenous), rectal, buccal (including sublingual), transdermal, and intranasal.

Pharmaceutically acceptable salts retain the desired biological activity of the parent polypeptide without toxic side effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalene disulfonic acids, polygalacturonic acid and the like; (b) base addition salts formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethylenediamine; or (c) combinations of (a) and (b), e.g., a zinc tannate salt and the like.

A further aspect of the present invention relates to pharmaceutical compositions comprising as an active ingredient a polypeptide of the present invention, or pharmaceutically acceptable salt thereof, in admixture with a pharmaceutically acceptable, non-toxic carrier. As mentioned above, such compositions may be prepared for parenteral (subcutaneous, intramuscular or intravenous) administration, particularly in the form of liquid solutions or suspensions; for oral or buccal administration, particularly in the form of tablets or capsules; for intranasal administration, particularly in the form of powders, nasal drops or aerosols; and for rectal or transdermal administration.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985), incorporated herein by reference. Formulations for parenteral administration may contain as excipients sterile water or saline, alkylene glycols such as propylene glycol, polyalkylene glycols such as polyethylene glycol, oils of vegetable origin, hydrogenated naphthalenes and the like. For oral administration, the formulation can be enhanced by the addition of bile salts or acylcarnitines. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

When formulated for nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent. An additional class of absorption enhancers exhibiting greater efficacy with decreased irritation is the class of alkyl maltosides, such as tetradecylmaltoside (Arnold, J J, et al. (2004). J Pharm. Sci. 93, 2205-13, and references therein, all of which are hereby incorporated by reference).

Delivery of the compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir-type microcapsules, depot implants, osmotic pumps, vesicles, micelies, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

One form of controlled release formulation contains the polypeptide or its salt dispersed or encapsulated in a slowly degrading, non-toxic, non-antigenic polymer such as copoly (lactic/glycolic) acid, as described in the pioneering work of Kent, Lewis, Sanders, and Tice, U.S. Pat. No. 4,675,189, incorporated by reference herein. The compounds or, preferably, their relatively insoluble salts, may also be formulated in cholesterol or other lipid matrix pellets, or silastomer matrix implants. Additional slow release, depot implant or injectable formulations will be apparent to the skilled artisan. See, for example, Sustained and Controlled Release Drug Delivery Systems, J. R. Robinson ed., Marcel Dekker, Inc., New York, 1978, and R. W. Baker, Controlled Release of Biologically Active Agents, John Wiley & Sons, New York, 1987, incorporated by reference herein.

All publications and patent applications mentioned in this specification are herein incorporated by reference to the same extent as if each independent publication or patent application was specifically and individually indicated to be incorporated by reference.

While the examples and discussion given above are intended to illustrate the synthesis and testing of representative compounds of the invention, it will be understood that it is capable of further modifications and should not be construed as limiting the scope of the appended claims.

REFERENCES

U.S. Pat. No. 5,589,452 (1996), Analogs of Parathyroid Hormone and Parathyroid Hormone Related peptide: Synthesis and Use for the Treatment of Osteoporosis. J. L. Krstenansky et al.

Arnold, J J, et al. (2004). Correlation of Tetradecylmaltoside Induced Increases in Nasal Peptide Drug Delivery with Morphological Changes in Nasal Epithelial Cells. J Pharm. Sci. 93, 2205-13

Yung, S L., et al. (2003) Generation of Highly Selective VPAC2 Receptor Agonists by High Throughput Mutagenesis of Vasoactive Intestinal Polypeptide and Pituitary Adenylate Cyclase-activating Peptide. J Biol Chem 278, 10273-81.

Tsutsumi, M., et al. (2002) A Potent and Highly Selective VPAC2 Agonist Enhances Glucose-Induced Insulin Release and Glucose Disposal. A Potential Therapy for Type 2 Diabetes. Diabetes 51, 1453-60.

Langer, I., et al. (2004) Hexanoylation of VPAC2 receptor-preferring ligand markedly increased its selectivity and potency. Peptides 25, 275-8.

Knudsen, L B, et al. (2000). Potent Derivatives of Glucagon-like Peptide-1 with Pharmacokinetic Properties Suitable for Once Daily Administration. J. Med. Chem. 43, 1664-9

Gourlet P, et al. (1997). The long-acting vasoactive intestinal polypeptide agonist RO 25-1553 is highly selective of the VIP2 receptor subclass. Peptides 18, 403-8

Gourlet P, et al. (1998). Interaction of lipophilic VIP derivatives with recombinant VIP1/PACAP and VIP2/PACAP receptors. Eur. J. Pharmacol. 354, 105-111

Greenwald R B, et al. (2003). Effective drug delivery by PEGylated drug conjugates. Adv. Drug Del. Rev. 55, 217-250

Nielsen L L, Young, A A, Parkes, D G (2004). Pharmacology of exenatide (synthetic exendin-4): a potential therapeutic for improved glycemic control of type 2 diabetes. Regul. Peptides 117, 77-88

Kieffer T J and Habener, J R (1999). The Glucagon-Like Peptides. Endocr. Rev. 20, 876-913

Knudsen, L B. (2004). Glucagon-like Peptide-1: The Basis of a New Class of Treatment for Type 2 Diabetes. J. Med. Chem. 47, 4128-34

Kurtzhals, P et al. (1995). Albumin binding of insulins acylated with fatty acids: characterization of the ligand-protein interaction and correlation between binding affinity and timing of the insulin effect in vivo. Biochem J. 312, 725-31.

Kurtzhals, P. (2004). Engineering predictability and protraction in a basal insulin analogue: the pharmacology of insulin detemir. Int. J. Obesity 28, Suppl 2, S23-8

Xia M, et al. (1997). Novel cyclic peptide agonist of high potency and selectivity for the type II vasoactive intestinal peptide receptor. J. Pharmacol. Exp. Ther. 281, 629-33

Deiters, A, et al. (2004). Site-specific PEGylation of proteins containing unnatural amino acids. Bio-org. Med. Chem. Lett. 14, 5743-5

What is claimed is:

1. A modified vasoactive intestinal polypeptide having the amino acid sequence of Acy-His-Ser-Asp-Ala-Val-Phe-Thr-Asp-Asn-Tyr-Thr-Arg-Leu-Arg-Lys-Gln-Val-Ala-Ala-Lys-Lys-Tyr-Leu-Asn-Trp-lle-Lys-Lys-Ala-Lys-Arg-Glu-Leu-Leu-Glu-Lys-Leu-Lys (ε-long acyl)-X(SEQ ID NO:6):

wherein:

Acyl is a $C_2$-$C_{16}$ acyl chain;

long acyl is a $C_6$-$C_{24}$ acyl chain;

X is OH or NHR1; and

R1 is H, lower alkyl, haloalkyl, or PEG.

2. The modified polypeptide of claim 1, wherein acyl is a $C_4$-$C_8$ acyl chain; long acyl is a $C_6$-$C_{14}$ acyl chain; and PEG is a polyethylene glycol chain of $C_2$-$C_{20}$.

3. A method for producing the modified polypeptide of claim 1, said method comprising synthesizing a polypeptide with the SEQ ID NO:6 by the sequential addition of protected amino acids from a peptide chain, removing the protecting groups, desalting and purifying the polypeptide.

4. A pharmaceutical composition comprising the modified polypeptide of claim 1, or acceptable salt thereof, and at least one pharmaceutically acceptable carrier or excipient.

5. The pharmaceutical composition of claim 4, further comprising at least one compound selected from the group consisting of insulin, insulin analogs, incretin, incretin analogs, glucagon-like peptide, glucagon-like peptide analogs, exendin, exendin analogs, sulfonylureas, biguanidase, α-gulocosidase inhibitors, thiazolidinediones, peroxisome proliferator activated receptor (PPAR) agonists, PPAR antagonists and PPAR partial agonists.

6. A modified vasoactive intestinal polypeptide having the amino acid sequence of Acy-His-Ser-Asp-Ala-Val-Phe-Thr-Asp-Asn-Tyr-Thr-Arg-Leu-Arg-Lys-Gln-Val-Ala-Ala-Lys-Lys-Tyr-Leu-Asn-Trp-lle-Lys-Lys-Ala-Lys-Arg-Glu-Leu-Leu-Glu-Lys-Leu-Lys (ε-long acyl)-X(SEQ ID NO:6):

wherein:

Acyl is a $C_5$ acyl chain;

long acyl is a $C_{18}$ acyl chain;

X is OH or NHR1; and

R1 is H, lower alkyl, haloalkyl, or PEG.

7. A method for producing the modified polypeptide of claim 6, said method comprising synthesizing a polypeptide with the SEQ ID NO:6 by the sequential addition of protected amino acids from a peptide chain, removing the protecting groups, desalting and purifying the polypeptide.

8. A pharmaceutical composition comprising the modified polypeptide of claim 6, or acceptable salt thereof, and at least one pharmaceutically acceptable carrier or excipient.

9. The pharmaceutical composition of claim 8, further comprising at least one compound selected from the group consisting of insulin, insulin analogs, incretin, incretin analogs, glucagon-like peptide, glucagon-like peptide analogs, exendin, exendin analogs, sulfonylureas, biguanidase, α-gulocosidase inhibitors, thiazolidinediones, peroxisome proliferator activated receptor (PPAR) agonists, PPAR antagonists and PPAR partial agonists.

* * * * *

UNITED STATES PATENT AND TRADEMARK OFFICE
CERTIFICATE OF CORRECTION

PATENT NO. : 7,566,691 B2
APPLICATION NO. : 11/245499
DATED : July 28, 2009
INVENTOR(S) : John Nestor It is certified that error appears in the above-identified patent and that said Letters Patent is hereby corrected as shown below:

Col. 93, Claim 5, lines 5-6, replace "α-gulocosidase" with -- α-glucosidase --.

Col. 94, Claim 9, lines 5-6, replace "α-gulocosidase" with -- α-glucosidase --.

Signed and Sealed this

Fifteenth Day of September, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,566,691 B2 | Page 1 of 1 |
| APPLICATION NO. | : 11/245499 | |
| DATED | : July 28, 2009 | |
| INVENTOR(S) | : John Nestor | |

It is certified that error appears in the above-identified patent and that said Letters Patent is hereby corrected as shown below:

Col. 93, Claim 5, lines 28-29, replace "α-gulocosidase" with -- α-glucosidase --.

Col. 94, Claim 9, lines 26-27, replace "α-gulocosidase" with -- α-glucosidase --.

This certificate supersedes the Certificate of Correction issued September 15, 2009.

Signed and Sealed this

Sixth Day of October, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,566,691 B2 | Page 1 of 1 |
| APPLICATION NO. | : 11/245499 | |
| DATED | : July 28, 2009 | |
| INVENTOR(S) | : Nestor | |

It is certified that error appears in the above-identified patent and that said Letters Patent is hereby corrected as shown below:

On the cover page,

[*] Notice:   Subject to any disclaimer, the term of this patent is extended or adjusted under 35 USC 154(b) by (216) days Delete the phrase "by 216 days" and insert -- by 510 days --

Signed and Sealed this

Fourth Day of May, 2010

David J. Kappos
*Director of the United States Patent and Trademark Office*

SEQUENCE LISTING

```
<160> NUMBER OF SEQ ID NOS: 64

<210> SEQ ID NO 1
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (38)..(38)
<223> OTHER INFORMATION: Lys(epsilon long acyl)

<400> SEQUENCE: 1

His Ser Asp Ala Val Phe Thr Asp Asn Tyr Thr Arg Leu Arg Lys Gln
1               5                   10                  15

Val Ala Ala Lys Lys Tyr Leu Asn Trp Ile Lys Lys Ala Lys Arg Glu
            20                  25                  30

Leu Leu Glu Lys Leu Lys
        35

<210> SEQ ID NO 2
<211> LENGTH: 42
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (42)..(42)
<223> OTHER INFORMATION: Lys(epsilon lauroyl)

<400> SEQUENCE: 2

His Ser Asp Ala Val Phe Thr Asp Asn Tyr Thr Arg Leu Arg Lys Gln
1               5                   10                  15

Val Ala Ala Lys Lys Tyr Leu Asn Ser Ile Lys Lys Gly Lys Arg Glu
            20                  25                  30
```

```
Leu Leu Glu Lys Leu Leu Arg Lys Leu Lys
        35                  40

<210> SEQ ID NO 3
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (38)..(38)
<223> OTHER INFORMATION: Lys(epsilon lauroyl)

<400> SEQUENCE: 3

His Ser Asp Ala Val Phe Thr Asp Asn Tyr Thr Arg Leu Arg Lys Gln
1               5                   10                  15

Val Ala Ala Lys Lys Tyr Leu Asn Ser Ile Lys Lys Gly Lys Arg Glu
            20                  25                  30

Leu Leu Glu Lys Leu Lys
        35

<210> SEQ ID NO 4
<211> LENGTH: 42
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (42)..(42)
<223> OTHER INFORMATION: Lys(epsilon lauroyl)

<400> SEQUENCE: 4

His Ser Asp Ala Val Phe Thr Asp Asn Tyr Thr Arg Leu Arg Lys Gln
1               5                   10                  15

Val Ala Ala Lys Lys Tyr Leu Asn Ser Ile Lys Lys Gly Lys Arg Glu
            20                  25                  30

Leu Leu Glu Lys Leu Leu Arg Lys Leu Lys
        35                  40

<210> SEQ ID NO 5
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (38)..(38)
<223> OTHER INFORMATION: Lys(epsilon myristoyl)

<400> SEQUENCE: 5

His Ser Asp Ala Val Phe Thr Asp Asn Tyr Thr Arg Leu Arg Lys Gln
1               5                   10                  15

Val Ala Ala Lys Lys Tyr Leu Asn Ser Ile Lys Lys Gly Lys Arg Glu
            20                  25                  30

Leu Leu Glu Lys Leu Lys
        35
```

<210> SEQ ID NO 6
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (38)..(38)
<223> OTHER INFORMATION: Lys(epsilon stearoyl)

<400> SEQUENCE: 6

His Ser Asp Ala Val Phe Thr Asp Asn Tyr Thr Arg Leu Arg Lys Gln
1               5                   10                  15

Val Ala Ala Lys Lys Tyr Leu Asn Trp Ile Lys Lys Ala Lys Arg Glu
            20                  25                  30

Leu Leu Glu Lys Leu Lys
        35

<210> SEQ ID NO 7
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (41)..(41)
<223> OTHER INFORMATION: Lys(epsilon stearoyl)

<400> SEQUENCE: 7

His Ser Asp Ala Val Phe Thr Asp Asn Tyr Thr Arg Leu Arg Lys Gln
1               5                   10                  15

Leu Ala Ala Lys Lys Tyr Leu Asn Ser Ile Lys Lys Gly Lys Arg Leu
            20                  25                  30

Leu Arg Lys Leu Gln Pro Pro Pro Lys
        35                  40

<210> SEQ ID NO 8
<211> LENGTH: 41
<212> TYPE: PRT
<213> ORGANISM: Artificial Sequence
<220> FEATURE:
<223> OTHER INFORMATION: synthetic peptide

<400> SEQUENCE: 8

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Lys Gly Lys Arg Glu
            20                  25                  30

Leu Leu Glu Lys Leu Leu Arg Lys Leu
        35                  40

<210> SEQ ID NO 9
<211> LENGTH: 44
<212> TYPE: PRT
<213> ORGANISM: Artificial Sequence

```
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acyl-His

<400> SEQUENCE: 9

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Lys Gly Lys Arg Glu
            20                  25                  30

Leu Leu Glu Lys Leu Leu Arg Lys Leu Pro Pro Pro
        35                  40

<210> SEQ ID NO 10
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acyl-His
<220> FEATURE:
<221> NAME/KEY: MISC_FEATURE
<222> LOCATION: (41)..(41)
<223> OTHER INFORMATION: Lys(epsilon long acyl)

<400> SEQUENCE: 10

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Lys Gly Lys Arg Glu
            20                  25                  30

Leu Leu Glu Arg Leu Leu Arg Lys Lys
        35                  40

<210> SEQ ID NO 11
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acyl-His

<400> SEQUENCE: 11

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Lys Gly Lys Arg Glu
            20                  25                  30

Leu Leu Glu Lys Leu Leu Arg Lys Leu
        35                  40

<210> SEQ ID NO 12
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acyl-His
```

```
<400> SEQUENCE: 12

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Gly Lys Arg Glu
            20                  25                  30

Leu Leu Glu Lys Leu Leu Arg Lys Leu
        35                  40

<210> SEQ ID NO 13
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (41)..(41)
<223> OTHER INFORMATION: Lys(epsilon long acyl)

<400> SEQUENCE: 13

His Ser Asp Ala Val Phe Thr Asp Asn Tyr Thr Arg Leu Arg Lys Gln
1               5                   10                  15

Met Ala Ala Lys Lys Tyr Leu Asn Ser Leu Lys Lys Gly Lys Arg Glu
            20                  25                  30

Leu Leu Glu Lys Leu Leu Arg Lys Lys
        35                  40

<210> SEQ ID NO 14
<211> LENGTH: 44
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Hexanoyl-His

<400> SEQUENCE: 14

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Lys Gly Lys Arg Glu
            20                  25                  30

Leu Leu Glu Lys Leu Leu Arg Lys Leu Pro Pro Pro
        35                  40

<210> SEQ ID NO 15
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Hexanoyl-His
<220> FEATURE:
<221> NAME/KEY: MISC_FEATURE
<222> LOCATION: (41)..(41)
<223> OTHER INFORMATION: Leu(PEG4)

<400> SEQUENCE: 15

His Ser Asp Ala Val Phe Thr Asp Asn Tyr Thr Arg Leu Arg Lys Gln
1               5                   10                  15
```

```
Met Ala Ala Lys Lys Tyr Leu Asn Ser Ile Lys Lys Gly Lys Arg Glu
            20                  25                  30

Leu Leu Glu Arg Leu Leu Arg Lys Leu
        35                  40

<210> SEQ ID NO 16
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Hexanoyl-His
<220> FEATURE:
<221> NAME/KEY: MISC_FEATURE
<222> LOCATION: (41)..(41)
<223> OTHER INFORMATION: Lys(C12)

<400> SEQUENCE: 16

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Lys Gly Lys Arg Glu
            20                  25                  30

Leu Leu Glu Lys Leu Leu Arg Lys Lys
        35                  40

<210> SEQ ID NO 17
<211> LENGTH: 44
<212> TYPE: PRT
<213> ORGANISM: Artificial Sequence
<220> FEATURE:
<223> OTHER INFORMATION: synthetic peptide

<400> SEQUENCE: 17

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Lys Gly Lys Arg Glu
            20                  25                  30

Leu Leu Glu Lys Leu Leu Arg Lys Leu Pro Pro Pro
        35                  40

<210> SEQ ID NO 18
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (41)..(41)
<223> OTHER INFORMATION: Leu(PEG4)

<400> SEQUENCE: 18

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Lys Gly Lys Arg Glu
            20                  25                  30

Leu Leu Glu Arg Leu Leu Arg Lys Leu
        35                  40

<210> SEQ ID NO 19
<211> LENGTH: 41
<212> TYPE: PRT
```

```
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (41)..(41)
<223> OTHER INFORMATION: Lys(C12)

<400> SEQUENCE: 19

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Lys Gly Lys Arg Glu
            20                  25                  30

Leu Leu Glu Lys Leu Leu Arg Lys Lys
        35                  40

<210> SEQ ID NO 20
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (38)..(38)
<223> OTHER INFORMATION: Lys(epsilon stearoyl)

<400> SEQUENCE: 20

His Ser Asp Ala Val Phe Thr Asp Asn Tyr Thr Arg Leu Arg Lys Gln
1               5                   10                  15

Val Ala Ala Lys Lys Tyr Leu Asn Ser Ile Lys Lys Ala Lys Arg Glu
            20                  25                  30

Leu Leu Glu Lys Leu Lys
        35

<210> SEQ ID NO 21
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (41)..(41)
<223> OTHER INFORMATION: Lys(epsilon stearoyl)

<400> SEQUENCE: 21

His Ser Asp Ala Val Phe Thr Arg Asn Tyr Thr Arg Leu Arg Arg Gln
1               5                   10                  15

Leu Ala Ala Arg Arg Tyr Leu Asn Ser Ile Lys Lys Ala Arg Arg Leu
            20                  25                  30

Leu Arg Arg Leu Leu Pro Pro Pro Lys
        35                  40

<210> SEQ ID NO 22
<211> LENGTH: 40
<212> TYPE: PRT
<213> ORGANISM: Artificial Sequence
<220> FEATURE:
```

<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (41)..(41)
<223> OTHER INFORMATION: Lys(epsilon stearoyl)

<400> SEQUENCE: 22

His Ser Asp Ala Val Phe Thr Arg Asn Tyr Thr Arg Leu Arg Arg Gln
1               5                   10                  15

Leu Ala Ala Arg Arg Tyr Leu Asn Ser Ile Lys Lys Ala Arg Arg Leu
            20                  25                  30

Leu Arg Arg Leu Gln Pro Pro Lys
        35                  40

<210> SEQ ID NO 23
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (41)..(41)
<223> OTHER INFORMATION: Lys(epsilon stearoyl)

<400> SEQUENCE: 23

His Ser Asp Ala Val Phe Thr Asp Asn Tyr Thr Arg Leu Arg Lys Gln
1               5                   10                  15

Leu Ala Ala Lys Lys Tyr Leu Asn Ser Ile Lys Lys Gly Lys Arg Leu
            20                  25                  30

Leu Arg Lys Leu Gln Pro Pro Pro Lys
        35                  40

<210> SEQ ID NO 24
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (38)..(38)
<223> OTHER INFORMATION: Lys(epsilon lauroyl)

<400> SEQUENCE: 24

His Ser Asp Ala Val Phe Thr Asp Asn Tyr Thr Arg Leu Arg Lys Gln
1               5                   10                  15

Val Ala Ala Lys Lys Tyr Leu Asn Ser Ile Lys Lys Gly Lys Arg Glu
            20                  25                  30

Leu Leu Glu Lys Leu Lys
        35

<210> SEQ ID NO 25
<211> LENGTH: 41
<212> TYPE: PRT

```
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (38)..(38)
<223> OTHER INFORMATION: Lys(epsilon myristoyl)

<400> SEQUENCE: 25

His Ser Asp Ala Val Phe Thr Asp Asn Tyr Thr Arg Leu Arg Lys Gln
1               5                   10                  15

Val Ala Ala Lys Lys Tyr Leu Asn Ser Ile Lys Lys Gly Lys Arg Glu
            20                  25                  30

Leu Leu Glu Lys Leu Lys Pro Pro Pro
        35                  40

<210> SEQ ID NO 26
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (41)..(41)
<223> OTHER INFORMATION: Lys(epsilon stearoyl)

<400> SEQUENCE: 26

His Ser Asp Ala Val Phe Thr Arg Asn Tyr Thr Arg Leu Arg Arg Gln
1               5                   10                  15

Leu Ala Ala Arg Arg Tyr Leu Asn Ser Ile Lys Lys Ala Arg Arg Leu
            20                  25                  30

Leu Arg Arg Leu Gln Pro Pro Pro Lys
        35                  40

<210> SEQ ID NO 27
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Hexanoyl-His
<220> FEATURE:
<221> NAME/KEY: MISC_FEATURE
<222> LOCATION: (41)..(41)
<223> OTHER INFORMATION: Lys(epsilon stearoyl)

<400> SEQUENCE: 27

His Ser Asp Ala Val Phe Thr Arg Asn Tyr Thr Arg Leu Arg Arg Gln
1               5                   10                  15

Leu Ala Ala Arg Arg Tyr Leu Asn Ser Ile Lys Lys Ala Arg Arg Leu
            20                  25                  30

Leu Glu Lys Leu Leu Arg Lys Leu Lys
        35                  40

<210> SEQ ID NO 28
```

```
<211> LENGTH: 44
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (41)..(41)
<223> OTHER INFORMATION: Lys(epsilon stearoyl)

<400> SEQUENCE: 28

His Ser Asp Ala Val Phe Thr Arg Asn Tyr Thr Arg Leu Arg Arg Gln
1               5                   10                  15

Leu Ala Ala Arg Arg Tyr Leu Asn Trp Ile Lys Lys Ala Arg Arg Leu
            20                  25                  30

Leu Glu Lys Leu Leu Arg Lys Leu Lys Pro Pro Pro
        35                  40

<210> SEQ ID NO 29
<211> LENGTH: 42
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (42)..(42)
<223> OTHER INFORMATION: Lys(epsilon stearoyl)

<400> SEQUENCE: 29

His Ser Asp Ala Val Phe Thr Arg Asn Tyr Thr Arg Leu Arg Arg Gln
1               5                   10                  15

Leu Ala Ala Arg Arg Tyr Leu Asn Trp Ile Lys Lys Ala Arg Arg Glu
            20                  25                  30

Leu Leu Glu Lys Leu Leu Arg Lys Leu Lys
        35                  40

<210> SEQ ID NO 30
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (37)..(37)
<223> OTHER INFORMATION: Lys(epsilon stearoyl)

<400> SEQUENCE: 30

His Ser Asp Ala Val Phe Thr Arg Asn Tyr Thr Arg Leu Arg Arg Gln
1               5                   10                  15

Leu Ala Ala Arg Arg Tyr Leu Asn Ser Ile Lys Lys Ala Arg Arg Leu
            20                  25                  30

Leu Glu Lys Leu Lys Pro Pro Pro
        35                  40
```

```
<210> SEQ ID NO 31
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (38)..(38)
<223> OTHER INFORMATION: Lys(epsilon stearoyl)

<400> SEQUENCE: 31

His Ser Asp Ala Val Phe Thr Asp Asn Tyr Thr Arg Leu Arg Lys Gln
1               5                   10                  15

Leu Ala Ala Lys Lys Tyr Leu Asn Trp Ile Lys Lys Ala Lys Arg Glu
            20                  25                  30

Leu Leu Glu Lys Leu Lys
        35

<210> SEQ ID NO 32
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (38)..(38)
<223> OTHER INFORMATION: Lys(epsilon stearoyl)

<400> SEQUENCE: 32

His Ser Asp Ala Val Phe Thr Asp Asn Tyr Thr Arg Leu Arg Lys Gln
1               5                   10                  15

Val Ala Ala Lys Lys Tyr Leu Asn Ser Ile Lys Lys Ala Lys Arg Glu
            20                  25                  30

Leu Leu Glu Lys Leu Lys
        35

<210> SEQ ID NO 33
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acyl-His
<220> FEATURE:
<221> NAME/KEY: MISC_FEATURE
<222> LOCATION: (38)..(38)
<223> OTHER INFORMATION: Lys(epsilon stearoyl)

<400> SEQUENCE: 33

His Ser Asp Ala Val Phe Thr Asp Asn Tyr Thr Arg Leu Arg Lys Gln
1               5                   10                  15

Val Ala Ala Lys Lys Tyr Leu Asn Trp Ile Lys Lys Ala Lys Arg Glu
            20                  25                  30

Leu Leu Glu Lys Leu Lys
```

-continued

```
<210> SEQ ID NO 34
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Propionyl-His
<220> FEATURE:
<221> NAME/KEY: MISC_FEATURE
<222> LOCATION: (38)..(38)
<223> OTHER INFORMATION: Lys(epsilon stearoyl)

<400> SEQUENCE: 34

His Ser Asp Ala Val Phe Thr Asp Asn Tyr Thr Arg Leu Arg Lys Gln
 1               5                  10                  15

Val Ala Ala Lys Lys Tyr Leu Asn Trp Ile Lys Lys Ala Lys Arg Glu
            20                  25                  30

Leu Leu Glu Lys Leu Lys
        35

<210> SEQ ID NO 35
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (38)..(38)
<223> OTHER INFORMATION: Lys(epsilon stearoyl)

<400> SEQUENCE: 35

His Ser Asp Ala Val Phe Thr Asp Asn Tyr Thr Arg Leu Arg Lys Gln
 1               5                  10                  15

Val Ala Ala Lys Lys Tyr Leu Asn Trp Ile Lys Arg Ala Lys Arg Glu
            20                  25                  30

Leu Leu Glu Lys Leu Lys
        35

<210> SEQ ID NO 36
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (41)..(41)
<223> OTHER INFORMATION: Lys(epsilon stearoyl)

<400> SEQUENCE: 36

His Ser Asp Ala Val Phe Thr Asp Asn Tyr Thr Arg Leu Arg Lys Gln
 1               5                  10                  15

Val Ala Ala Lys Lys Tyr Leu Asn Trp Ile Lys Lys Gly Lys Arg Leu
            20                  25                  30
```

Leu Arg Lys Leu Gly Pro Pro Pro Lys
        35              40

<210> SEQ ID NO 37
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (41)..(41)
<223> OTHER INFORMATION: Lys(epsilon stearoyl)

<400> SEQUENCE: 37

His Ser Asp Ala Val Phe Thr Asp Asn Tyr Thr Arg Leu Arg Lys Gln
1               5                   10                  15

Val Ala Ala Lys Lys Tyr Leu Asn Trp Ile Lys Lys Gly Lys Arg Leu
            20                  25                  30

Leu Arg Lys Leu Ala Pro Pro Lys
        35              40

<210> SEQ ID NO 38
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Pentanoyl-His
<220> FEATURE:
<221> NAME/KEY: MISC_FEATURE
<222> LOCATION: (41)..(41)
<223> OTHER INFORMATION: Lys(epsilon stearoyl)

<400> SEQUENCE: 38

His Ser Asp Ala Val Phe Thr Asp Asn Tyr Thr Arg Leu Arg Lys Gln
1               5                   10                  15

Val Ala Ala Lys Lys Tyr Leu Asn Trp Ile Lys Lys Gly Lys Arg Leu
            20                  25                  30

Leu Arg Lys Leu Gln Pro Pro Lys
        35              40

<210> SEQ ID NO 39
<211> LENGTH: 30
<212> TYPE: PRT
<213> ORGANISM: Artificial Sequence
<220> FEATURE:
<223> OTHER INFORMATION: synthetic peptide

<400> SEQUENCE: 39

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 40
<211> LENGTH: 38
<212> TYPE: PRT
<213> ORGANISM: Artificial Sequence -continued

```
<220> FEATURE:
<223> OTHER INFORMATION: synthetic peptide

<400> SEQUENCE: 40

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 41
<211> LENGTH: 44
<212> TYPE: PRT
<213> ORGANISM: Artificial Sequence
<220> FEATURE:
<223> OTHER INFORMATION: synthetic peptide

<400> SEQUENCE: 41

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 42
<211> LENGTH: 38
<212> TYPE: PRT
<213> ORGANISM: Artificial Sequence
<220> FEATURE:
<223> OTHER INFORMATION: synthetic peptide

<400> SEQUENCE: 42

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 43
<211> LENGTH: 38
<212> TYPE: PRT
<213> ORGANISM: Artificial Sequence
<220> FEATURE:
<223> OTHER INFORMATION: synthetic peptide

<400> SEQUENCE: 43

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn Gly Lys Arg Ser
            20                  25                  30

Ser Glu Gly Glu Ser Pro
        35

<210> SEQ ID NO 44
<211> LENGTH: 31
<212> TYPE: PRT
<213> ORGANISM: Artificial Sequence
<220> FEATURE:
<223> OTHER INFORMATION: synthetic peptide
```

```
<400> SEQUENCE: 44

His Ser Asp Ala Val Phe Thr Asp Asn Tyr Thr Arg Leu Arg Lys Gln
1               5                   10                  15

Val Ala Ala Lys Lys Tyr Leu Gln Ser Ile Lys Asn Lys Arg Tyr
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: synthetic peptide

<400> SEQUENCE: 45

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Arg
            20                  25                  30

<210> SEQ ID NO 46
<211> LENGTH: 30
<212> TYPE: PRT
<213> ORGANISM: Artificial Sequence
<220> FEATURE:
<223> OTHER INFORMATION: synthetic peptide

<400> SEQUENCE: 46

His Ser Asp Ala Val Phe Thr Asp Asn Tyr Thr Arg Leu Arg Lys Gln
1               5                   10                  15

Met Ala Ala Lys Lys Tyr Leu Asn Ser Ile Gln Asn Arg Arg
            20                  25                  30

<210> SEQ ID NO 47
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Hexanoyl-His

<400> SEQUENCE: 47

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Lys Gly Lys Arg Ser
            20                  25                  30

Ser Glu Gly Glu Ser Pro
        35

<210> SEQ ID NO 48
<211> LENGTH: 44
<212> TYPE: PRT
<213> ORGANISM: Artificial Sequence
<220> FEATURE:
<223> OTHER INFORMATION: synthetic peptide

<400> SEQUENCE: 48

His Ser Asp Ala Val Phe Thr Asp Asn Tyr Thr Arg Leu Arg Lys Gln
1               5                   10                  15

Val Ala Ala Lys Lys Tyr Leu Gln Ser Ile Lys Gln Lys Arg Tyr Glu
            20                  25                  30
```

```
Leu Leu Glu Lys Leu Leu Arg Lys Leu Arg Thr Ala
        35                  40
```

<210> SEQ ID NO 49
<211> LENGTH: 43
<212> TYPE: PRT
<213> ORGANISM: Artificial Sequence
<220> FEATURE:
<223> OTHER INFORMATION: synthetic peptide

<400> SEQUENCE: 49

```
His Ser Asp Ala Val Phe Thr Asp Asn Tyr Thr Arg Leu Arg Lys Gln
1               5                   10                  15

Val Ala Ala Lys Lys Tyr Leu Gln Ser Ile Lys Gln Lys Arg Glu Leu
            20                  25                  30

Leu Glu Lys Leu Leu Arg Lys Leu Arg Thr Ala
        35                  40
```

<210> SEQ ID NO 50
<211> LENGTH: 35
<212> TYPE: PRT
<213> ORGANISM: Artificial Sequence
<220> FEATURE:
<223> OTHER INFORMATION: synthetic peptide

<400> SEQUENCE: 50

```
His Ser Asp Ala Val Phe Thr Asp Asn Tyr Thr Arg Leu Arg Lys Gln
1               5                   10                  15

Val Ala Ala Lys Lys Tyr Leu Gln Ser Ile Leu Gly Ser Arg Thr Ser
            20                  25                  30

Pro Pro Pro
        35
```

<210> SEQ ID NO 51
<211> LENGTH: 42
<212> TYPE: PRT
<213> ORGANISM: Artificial Sequence
<220> FEATURE:
<223> OTHER INFORMATION: synthetic peptide

<400> SEQUENCE: 51

```
Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Thr Ile Gln
        35                  40
```

<210> SEQ ID NO 52
<211> LENGTH: 35
<212> TYPE: PRT
<213> ORGANISM: Artificial Sequence
<220> FEATURE:
<223> OTHER INFORMATION: synthetic peptide

<400> SEQUENCE: 52

```
His Ser Asp Ala Ile Phe Thr Gln Gln Tyr Ser Lys Leu Leu Ala Lys
1               5                   10                  15

Leu Ala Leu Gln Lys Tyr Leu Ala Ser Ile Leu Gly Ser Arg Thr Ser
            20                  25                  30

Pro Pro Pro
        35
```

```
<210> SEQ ID NO 53
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acyl-His
<220> FEATURE:
<221> NAME/KEY: MISC_FEATURE
<222> LOCATION: (4)..(4)
<223> OTHER INFORMATION: can be Gly or Ala
<220> FEATURE:
<221> NAME/KEY: MISC_FEATURE
<222> LOCATION: (5)..(5)
<223> OTHER INFORMATION: can be Val, Ile or Leu
<220> FEATURE:
<221> NAME/KEY: MISC_FEATURE
<222> LOCATION: (8)..(8)
<223> OTHER INFORMATION: can be Asp or Arg
<220> FEATURE:
<221> NAME/KEY: MISC_FEATURE
<222> LOCATION: (9)..(9)
<223> OTHER INFORMATION: can be Ser or Asn
<220> FEATURE:
<221> NAME/KEY: MISC_FEATURE
<222> LOCATION: (11)..(11)
<223> OTHER INFORMATION: can be Ser or Thr
<220> FEATURE:
<221> NAME/KEY: MISC_FEATURE
<222> LOCATION: (13)..(13)
<223> OTHER INFORMATION: can be Leu or Tyr
<220> FEATURE:
<221> NAME/KEY: MISC_FEATURE
<222> LOCATION: (17)..(17)
<223> OTHER INFORMATION: can be Met, Leu or Val
<220> FEATURE:
<221> NAME/KEY: MISC_FEATURE
<222> LOCATION: (19)..(19)
<223> OTHER INFORMATION: can be Ala or Val
<220> FEATURE:
<221> NAME/KEY: MISC_FEATURE
<222> LOCATION: (24)..(24)
<223> OTHER INFORMATION: can be Asn, Gln or Ala
<220> FEATURE:
<221> NAME/KEY: MISC_FEATURE
<222> LOCATION: (25)..(25)
<223> OTHER INFORMATION: can be Trp, Ala or Ser
<220> FEATURE:
<221> NAME/KEY: MISC_FEATURE
<222> LOCATION: (26)..(26)
<223> OTHER INFORMATION: can be Ile or Val
<220> FEATURE:
<221> NAME/KEY: MISC_FEATURE
<222> LOCATION: (27)..(27)
<223> OTHER INFORMATION: can be Leu or Lys
<220> FEATURE:
<221> NAME/KEY: MISC_FEATURE
<222> LOCATION: (28)..(28)
<223> OTHER INFORMATION: can be Lys, Arg, Asn or Gly
<220> FEATURE:
<221> NAME/KEY: MISC_FEATURE
<222> LOCATION: (29)..(29)
<223> OTHER INFORMATION: can be Ala or Gly
<220> FEATURE:
<221> NAME/KEY: MISC_FEATURE
<222> LOCATION: (30)..(30)
<223> OTHER INFORMATION: can be Lys or Arg
<220> FEATURE:
<221> NAME/KEY: MISC_FEATURE
<222> LOCATION: (31)..(31)
<223> OTHER INFORMATION: can be Lys or Arg
<220> FEATURE:
<221> NAME/KEY: MISC_FEATURE
<222> LOCATION: (32)..(32)
<223> OTHER INFORMATION: is a Hydrophilic amino acid
```

```
<220> FEATURE:
<221> NAME/KEY: MISC_FEATURE
<222> LOCATION: (33)..(33)
<223> OTHER INFORMATION: is a Lipophilic amino acid
<220> FEATURE:
<221> NAME/KEY: MISC_FEATURE
<222> LOCATION: (34)..(34)
<223> OTHER INFORMATION: is a Lipophilic amino acid
<220> FEATURE:
<221> NAME/KEY: MISC_FEATURE
<222> LOCATION: (35)..(35)
<223> OTHER INFORMATION: is a Hydrophilic amino acid
<220> FEATURE:
<221> NAME/KEY: MISC_FEATURE
<222> LOCATION: (36)..(36)
<223> OTHER INFORMATION: is a Hydrophilic amino acid
<220> FEATURE:
<221> NAME/KEY: MISC_FEATURE
<222> LOCATION: (37)..(37)
<223> OTHER INFORMATION: is a Lipophilic amino acid
<220> FEATURE:
<221> NAME/KEY: MISC_FEATURE
<222> LOCATION: (38)..(38)
<223> OTHER INFORMATION: Lys(epsilon long acyl)

<400> SEQUENCE: 53

His Ser Asp Xaa Xaa Phe Thr Xaa Xaa Tyr Xaa Arg Xaa Arg Lys Gln
1               5                   10                  15

Xaa Ala Xaa Lys Lys Tyr Leu Xaa Xaa Xaa Xaa Xaa Xaa Xaa Xaa
            20                  25                  30

Xaa Xaa Xaa Xaa Xaa Lys
        35

<210> SEQ ID NO 54
<211> LENGTH: 42
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acyl-His
<220> FEATURE:
<221> NAME/KEY: MISC_FEATURE
<222> LOCATION: (4)..(4)
<223> OTHER INFORMATION: can be Gly or Ala
<220> FEATURE:
<221> NAME/KEY: MISC_FEATURE
<222> LOCATION: (5)..(5)
<223> OTHER INFORMATION: can be Val, Ile or Leu
<220> FEATURE:
<221> NAME/KEY: MISC_FEATURE
<222> LOCATION: (8)..(8)
<223> OTHER INFORMATION: can be Asp or Arg
<220> FEATURE:
<221> NAME/KEY: MISC_FEATURE
<222> LOCATION: (9)..(9)
<223> OTHER INFORMATION: can be Ser or Asn
<220> FEATURE:
<221> NAME/KEY: MISC_FEATURE
<222> LOCATION: (11)..(11)
<223> OTHER INFORMATION: can be Ser or Thr
<220> FEATURE:
<221> NAME/KEY: MISC_FEATURE
<222> LOCATION: (13)..(13)
<223> OTHER INFORMATION: can be Leu or Tyr
<220> FEATURE:
<221> NAME/KEY: MISC_FEATURE
<222> LOCATION: (17)..(17)
<223> OTHER INFORMATION: can be Met, Leu or Val
<220> FEATURE:
<221> NAME/KEY: MISC_FEATURE
<222> LOCATION: (19)..(19)
<223> OTHER INFORMATION: can be Ala or Val
```

```
-continued

<220> FEATURE:
<221> NAME/KEY: MISC_FEATURE
<222> LOCATION: (24)..(24)
<223> OTHER INFORMATION: can be Asn, Gln or Ala
<220> FEATURE:
<221> NAME/KEY: MISC_FEATURE
<222> LOCATION: (25)..(25)
<223> OTHER INFORMATION: can be Trp, Ala or Ser
<220> FEATURE:
<221> NAME/KEY: MISC_FEATURE
<222> LOCATION: (26)..(26)
<223> OTHER INFORMATION: can be Ile or Val
<220> FEATURE:
<221> NAME/KEY: MISC_FEATURE
<222> LOCATION: (27)..(27)
<223> OTHER INFORMATION: can be Leu or Lys
<220> FEATURE:
<221> NAME/KEY: MISC_FEATURE
<222> LOCATION: (28)..(28)
<223> OTHER INFORMATION: can be Lys, Arg, Asn or Gly
<220> FEATURE:
<221> NAME/KEY: MISC_FEATURE
<222> LOCATION: (29)..(29)
<223> OTHER INFORMATION: can be Ala or Gly
<220> FEATURE:
<221> NAME/KEY: MISC_FEATURE
<222> LOCATION: (30)..(30)
<223> OTHER INFORMATION: can be Lys or Arg
<220> FEATURE:
<221> NAME/KEY: MISC_FEATURE
<222> LOCATION: (31)..(31)
<223> OTHER INFORMATION: can be Lys or Arg
<220> FEATURE:
<221> NAME/KEY: MISC_FEATURE
<222> LOCATION: (32)..(32)
<223> OTHER INFORMATION: is a Hydrophilic amino acid
<220> FEATURE:
<221> NAME/KEY: MISC_FEATURE
<222> LOCATION: (33)..(33)
<223> OTHER INFORMATION: is a Lipophilic amino acid
<220> FEATURE:
<221> NAME/KEY: MISC_FEATURE
<222> LOCATION: (34)..(34)
<223> OTHER INFORMATION: is a Lipophilic amino acid
<220> FEATURE:
<221> NAME/KEY: MISC_FEATURE
<222> LOCATION: (35)..(35)
<223> OTHER INFORMATION: is a Hydrophilic amino acid
<220> FEATURE:
<221> NAME/KEY: MISC_FEATURE
<222> LOCATION: (36)..(36)
<223> OTHER INFORMATION: is a Hydrophilic amino acid
<220> FEATURE:
<221> NAME/KEY: MISC_FEATURE
<222> LOCATION: (37)..(37)
<223> OTHER INFORMATION: is a Lipophilic amino acid
<220> FEATURE:
<221> NAME/KEY: MISC_FEATURE
<222> LOCATION: (38)..(38)
<223> OTHER INFORMATION: is a Lipophilic amino acid
<220> FEATURE:
<221> NAME/KEY: MISC_FEATURE
<222> LOCATION: (39)..(39)
<223> OTHER INFORMATION: is a Hydrophilic amino acid
<220> FEATURE:
<221> NAME/KEY: MISC_FEATURE
<222> LOCATION: (40)..(40)
<223> OTHER INFORMATION: is a Hydrophilic amino acid
<220> FEATURE:
<221> NAME/KEY: MISC_FEATURE
<222> LOCATION: (41)..(41)
<223> OTHER INFORMATION: is a Lipophilic amino acid
<220> FEATURE:
<221> NAME/KEY: MISC_FEATURE
<222> LOCATION: (42)..(42)
<223> OTHER INFORMATION: Lys(epsilon long acyl)

<400> SEQUENCE: 54
```

```
His Ser Asp Xaa Xaa Phe Thr Xaa Xaa Tyr Xaa Arg Xaa Arg Lys Gln
1               5                   10                  15

Xaa Ala Xaa Lys Lys Tyr Leu Xaa Xaa Xaa Xaa Xaa Xaa Xaa
            20                  25                  30

Xaa Xaa Xaa Xaa Xaa Xaa Xaa Xaa Xaa Lys
        35                  40
```

<210> SEQ ID NO 55
<211> LENGTH: 46
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acyl-His
<220> FEATURE:
<221> NAME/KEY: MISC_FEATURE
<222> LOCATION: (4)..(4)
<223> OTHER INFORMATION: can be Gly or Ala
<220> FEATURE:
<221> NAME/KEY: MISC_FEATURE
<222> LOCATION: (5)..(5)
<223> OTHER INFORMATION: can be Val, Ile or Leu
<220> FEATURE:
<221> NAME/KEY: MISC_FEATURE
<222> LOCATION: (8)..(8)
<223> OTHER INFORMATION: can be Asp or Arg
<220> FEATURE:
<221> NAME/KEY: MISC_FEATURE
<222> LOCATION: (9)..(9)
<223> OTHER INFORMATION: can be Ser or Asn
<220> FEATURE:
<221> NAME/KEY: MISC_FEATURE
<222> LOCATION: (11)..(11)
<223> OTHER INFORMATION: can be Ser or Thr
<220> FEATURE:
<221> NAME/KEY: MISC_FEATURE
<222> LOCATION: (13)..(13)
<223> OTHER INFORMATION: can be Leu or Tyr
<220> FEATURE:
<221> NAME/KEY: MISC_FEATURE
<222> LOCATION: (17)..(17)
<223> OTHER INFORMATION: can be Met, Leu or Val
<220> FEATURE:
<221> NAME/KEY: MISC_FEATURE
<222> LOCATION: (19)..(19)
<223> OTHER INFORMATION: can be Ala or Val
<220> FEATURE:
<221> NAME/KEY: MISC_FEATURE
<222> LOCATION: (24)..(24)
<223> OTHER INFORMATION: can be Asn, Gln or Ala
<220> FEATURE:
<221> NAME/KEY: MISC_FEATURE
<222> LOCATION: (25)..(25)
<223> OTHER INFORMATION: can be Trp, Ala or Ser
<220> FEATURE:
<221> NAME/KEY: MISC_FEATURE
<222> LOCATION: (26)..(26)
<223> OTHER INFORMATION: can be Ile or Val
<220> FEATURE:
<221> NAME/KEY: MISC_FEATURE
<222> LOCATION: (27)..(27)
<223> OTHER INFORMATION: can be Leu or Lys
<220> FEATURE:
<221> NAME/KEY: MISC_FEATURE
<222> LOCATION: (28)..(28)
<223> OTHER INFORMATION: can be Lys, Arg, Asn or Gly
<220> FEATURE:
<221> NAME/KEY: MISC_FEATURE
<222> LOCATION: (29)..(29)
<223> OTHER INFORMATION: can be Ala or Gly
<220> FEATURE:
<221> NAME/KEY: MISC_FEATURE
<222> LOCATION: (30)..(30)

```
<223> OTHER INFORMATION: can be Lys or Arg
<220> FEATURE:
<221> NAME/KEY: MISC_FEATURE
<222> LOCATION: (31)..(31)
<223> OTHER INFORMATION: can be Lys or Arg
<220> FEATURE:
<221> NAME/KEY: MISC_FEATURE
<222> LOCATION: (32)..(32)
<223> OTHER INFORMATION: is a Hydrophilic amino acid
<220> FEATURE:
<221> NAME/KEY: MISC_FEATURE
<222> LOCATION: (33)..(33)
<223> OTHER INFORMATION: is a Lipophilic amino acid
<220> FEATURE:
<221> NAME/KEY: MISC_FEATURE
<222> LOCATION: (34)..(34)
<223> OTHER INFORMATION: is a Lipophilic amino acid
<220> FEATURE:
<221> NAME/KEY: MISC_FEATURE
<222> LOCATION: (35)..(35)
<223> OTHER INFORMATION: is a Hydrophilic amino acid
<220> FEATURE:
<221> NAME/KEY: MISC_FEATURE
<222> LOCATION: (36)..(36)
<223> OTHER INFORMATION: is a Hydrophilic amino acid
<220> FEATURE:
<221> NAME/KEY: MISC_FEATURE
<222> LOCATION: (37)..(37)
<223> OTHER INFORMATION: is a Lipophilic amino acid
<220> FEATURE:
<221> NAME/KEY: MISC_FEATURE
<222> LOCATION: (38)..(38)
<223> OTHER INFORMATION: is a Lipophilic amino acid
<220> FEATURE:
<221> NAME/KEY: MISC_FEATURE
<222> LOCATION: (39)..(39)
<223> OTHER INFORMATION: is a Hydrophilic amino acid
<220> FEATURE:
<221> NAME/KEY: MISC_FEATURE
<222> LOCATION: (40)..(40)
<223> OTHER INFORMATION: is a Hydrophilic amino acid
<220> FEATURE:
<221> NAME/KEY: MISC_FEATURE
<222> LOCATION: (41)..(41)
<223> OTHER INFORMATION: is a Lipophilic amino acid
<220> FEATURE:
<221> NAME/KEY: MISC_FEATURE
<222> LOCATION: (42)..(42)
<223> OTHER INFORMATION: is a Lipophilic amino acid
<220> FEATURE:
<221> NAME/KEY: MISC_FEATURE
<222> LOCATION: (43)..(43)
<223> OTHER INFORMATION: is a Hydrophilic amino acid
<220> FEATURE:
<221> NAME/KEY: MISC_FEATURE
<222> LOCATION: (44)..(44)
<223> OTHER INFORMATION: is a Hydrophilic amino acid
<220> FEATURE:
<221> NAME/KEY: MISC_FEATURE
<222> LOCATION: (45)..(45)
<223> OTHER INFORMATION: is a Lipophilic amino acid
<220> FEATURE:
<221> NAME/KEY: MISC_FEATURE
<222> LOCATION: (46)..(46)
<223> OTHER INFORMATION: Lys(epsilon long acyl)

<400> SEQUENCE: 55

His Ser Asp Xaa Xaa Phe Thr Xaa Xaa Tyr Xaa Arg Xaa Arg Lys Gln
1               5                   10                  15

Xaa Ala Xaa Lys Lys Tyr Leu Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Lys
        35                  40                  45

<210> SEQ ID NO 56
```

```
<211> LENGTH: 42
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acyl-His
<220> FEATURE:
<221> NAME/KEY: MISC_FEATURE
<222> LOCATION: (4)..(4)
<223> OTHER INFORMATION: can be Gly or Ala
<220> FEATURE:
<221> NAME/KEY: MISC_FEATURE
<222> LOCATION: (5)..(5)
<223> OTHER INFORMATION: can be Val, Ile or Leu
<220> FEATURE:
<221> NAME/KEY: MISC_FEATURE
<222> LOCATION: (8)..(8)
<223> OTHER INFORMATION: can be Asp or Arg
<220> FEATURE:
<221> NAME/KEY: MISC_FEATURE
<222> LOCATION: (9)..(9)
<223> OTHER INFORMATION: can be Ser or Asn
<220> FEATURE:
<221> NAME/KEY: MISC_FEATURE
<222> LOCATION: (11)..(11)
<223> OTHER INFORMATION: can be Ser or Thr
<220> FEATURE:
<221> NAME/KEY: MISC_FEATURE
<222> LOCATION: (13)..(13)
<223> OTHER INFORMATION: can be Leu or Tyr
<220> FEATURE:
<221> NAME/KEY: MISC_FEATURE
<222> LOCATION: (17)..(17)
<223> OTHER INFORMATION: can be Met, Leu or Val
<220> FEATURE:
<221> NAME/KEY: MISC_FEATURE
<222> LOCATION: (19)..(19)
<223> OTHER INFORMATION: can be Ala or Val
<220> FEATURE:
<221> NAME/KEY: MISC_FEATURE
<222> LOCATION: (24)..(24)
<223> OTHER INFORMATION: can be Asn, Gln or Ala
<220> FEATURE:
<221> NAME/KEY: MISC_FEATURE
<222> LOCATION: (25)..(25)
<223> OTHER INFORMATION: can be Trp, Ala or Ser
<220> FEATURE:
<221> NAME/KEY: MISC_FEATURE
<222> LOCATION: (26)..(26)
<223> OTHER INFORMATION: can be Ile or Val
<220> FEATURE:
<221> NAME/KEY: MISC_FEATURE
<222> LOCATION: (27)..(27)
<223> OTHER INFORMATION: can be Leu or Lys
<220> FEATURE:
<221> NAME/KEY: MISC_FEATURE
<222> LOCATION: (28)..(28)
<223> OTHER INFORMATION: can be Lys, Arg, Asn or Gly
<220> FEATURE:
<221> NAME/KEY: MISC_FEATURE
<222> LOCATION: (29)..(29)
<223> OTHER INFORMATION: can be Ala or Gly
<220> FEATURE:
<221> NAME/KEY: MISC_FEATURE
<222> LOCATION: (30)..(30)
<223> OTHER INFORMATION: can be Lys or Arg
<220> FEATURE:
<221> NAME/KEY: MISC_FEATURE
<222> LOCATION: (31)..(31)
<223> OTHER INFORMATION: can be Lys or Arg
<220> FEATURE:
<221> NAME/KEY: MISC_FEATURE
<222> LOCATION: (32)..(32)
<223> OTHER INFORMATION: is a Hydrophilic amino acid
<220> FEATURE:
<221> NAME/KEY: MISC_FEATURE
```

```
<222> LOCATION: (33)..(33)
<223> OTHER INFORMATION: is a Lipophilic amino acid
<220> FEATURE:
<221> NAME/KEY: MISC_FEATURE
<222> LOCATION: (34)..(34)
<223> OTHER INFORMATION: is a Lipophilic amino acid
<220> FEATURE:
<221> NAME/KEY: MISC_FEATURE
<222> LOCATION: (35)..(35)
<223> OTHER INFORMATION: is a Hydrophilic amino acid
<220> FEATURE:
<221> NAME/KEY: MISC_FEATURE
<222> LOCATION: (36)..(36)
<223> OTHER INFORMATION: is a Hydrophilic amino acid
<220> FEATURE:
<221> NAME/KEY: MISC_FEATURE
<222> LOCATION: (37)..(37)
<223> OTHER INFORMATION: is a Lipophilic amino acid
<220> FEATURE:
<221> NAME/KEY: MISC_FEATURE
<222> LOCATION: (42)..(42)
<223> OTHER INFORMATION: Lys(epsilon long acyl)

<400> SEQUENCE: 56

His Ser Asp Xaa Xaa Phe Thr Xaa Xaa Tyr Xaa Arg Xaa Arg Lys Gln
 1               5                  10                  15

Xaa Ala Xaa Lys Lys Tyr Leu Xaa Xaa Xaa Xaa Xaa Xaa Xaa Xaa Xaa
            20                  25                  30

Xaa Xaa Xaa Xaa Xaa Gln Pro Pro Pro Lys
        35                  40

<210> SEQ ID NO 57
<211> LENGTH: 46
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acyl-His
<220> FEATURE:
<221> NAME/KEY: MISC_FEATURE
<222> LOCATION: (4)..(4)
<223> OTHER INFORMATION: can be Gly or Ala
<220> FEATURE:
<221> NAME/KEY: MISC_FEATURE
<222> LOCATION: (5)..(5)
<223> OTHER INFORMATION: can be Val, Ile or Leu
<220> FEATURE:
<221> NAME/KEY: MISC_FEATURE
<222> LOCATION: (8)..(8)
<223> OTHER INFORMATION: can be Asp or Arg
<220> FEATURE:
<221> NAME/KEY: MISC_FEATURE
<222> LOCATION: (9)..(9)
<223> OTHER INFORMATION: can be Ser or Asn
<220> FEATURE:
<221> NAME/KEY: MISC_FEATURE
<222> LOCATION: (11)..(11)
<223> OTHER INFORMATION: can be Ser or Thr
<220> FEATURE:
<221> NAME/KEY: MISC_FEATURE
<222> LOCATION: (13)..(13)
<223> OTHER INFORMATION: can be Leu or Tyr
<220> FEATURE:
<221> NAME/KEY: MISC_FEATURE
<222> LOCATION: (17)..(17)
<223> OTHER INFORMATION: can be Met, Leu or Val
<220> FEATURE:
<221> NAME/KEY: MISC_FEATURE
<222> LOCATION: (19)..(19)
<223> OTHER INFORMATION: can be Ala or Val
<220> FEATURE:
<221> NAME/KEY: MISC_FEATURE
```

```
<222> LOCATION: (24)..(24)
<223> OTHER INFORMATION: can be Asn, Gln or Ala
<220> FEATURE:
<221> NAME/KEY: MISC_FEATURE
<222> LOCATION: (25)..(25)
<223> OTHER INFORMATION: can be Trp, Ala or Ser
<220> FEATURE:
<221> NAME/KEY: MISC_FEATURE
<222> LOCATION: (26)..(26)
<223> OTHER INFORMATION: can be Ile or Val
<220> FEATURE:
<221> NAME/KEY: MISC_FEATURE
<222> LOCATION: (27)..(27)
<223> OTHER INFORMATION: can be Leu or Lys
<220> FEATURE:
<221> NAME/KEY: MISC_FEATURE
<222> LOCATION: (28)..(28)
<223> OTHER INFORMATION: can be Lys, Arg, Asn or Gly
<220> FEATURE:
<221> NAME/KEY: MISC_FEATURE
<222> LOCATION: (29)..(29)
<223> OTHER INFORMATION: can be Ala or Gly
<220> FEATURE:
<221> NAME/KEY: MISC_FEATURE
<222> LOCATION: (30)..(30)
<223> OTHER INFORMATION: can be Lys or Arg
<220> FEATURE:
<221> NAME/KEY: MISC_FEATURE
<222> LOCATION: (31)..(31)
<223> OTHER INFORMATION: can be Lys or Arg
<220> FEATURE:
<221> NAME/KEY: MISC_FEATURE
<222> LOCATION: (32)..(32)
<223> OTHER INFORMATION: is a Hydrophilic amino acid
<220> FEATURE:
<221> NAME/KEY: MISC_FEATURE
<222> LOCATION: (33)..(33)
<223> OTHER INFORMATION: is a Lipophilic amino acid
<220> FEATURE:
<221> NAME/KEY: MISC_FEATURE
<222> LOCATION: (34)..(34)
<223> OTHER INFORMATION: is a Lipophilic amino acid
<220> FEATURE:
<221> NAME/KEY: MISC_FEATURE
<222> LOCATION: (35)..(35)
<223> OTHER INFORMATION: is a Hydrophilic amino acid
<220> FEATURE:
<221> NAME/KEY: MISC_FEATURE
<222> LOCATION: (36)..(36)
<223> OTHER INFORMATION: is a Hydrophilic amino acid
<220> FEATURE:
<221> NAME/KEY: MISC_FEATURE
<222> LOCATION: (37)..(37)
<223> OTHER INFORMATION: is a Lipophilic amino acid
<220> FEATURE:
<221> NAME/KEY: MISC_FEATURE
<222> LOCATION: (38)..(38)
<223> OTHER INFORMATION: is a Lipophilic amino acid
<220> FEATURE:
<221> NAME/KEY: MISC_FEATURE
<222> LOCATION: (39)..(39)
<223> OTHER INFORMATION: is a Hydrophilic amino acid
<220> FEATURE:
<221> NAME/KEY: MISC_FEATURE
<222> LOCATION: (40)..(40)
<223> OTHER INFORMATION: is a Hydrophilic amino acid
<220> FEATURE:
<221> NAME/KEY: MISC_FEATURE
<222> LOCATION: (41)..(41)
<223> OTHER INFORMATION: is a Lipophilic amino acid
<220> FEATURE:
<221> NAME/KEY: MISC_FEATURE
<222> LOCATION: (46)..(46)
<223> OTHER INFORMATION: Lys(epsilon long acyl)

<400> SEQUENCE: 57

His Ser Asp Xaa Xaa Phe Thr Xaa Xaa Tyr Xaa Arg Xaa Arg Lys Gln
 1               5                  10                  15
```

Xaa Ala Xaa Lys Lys Tyr Leu Xaa Xaa Xaa Xaa Xaa Xaa Xaa Xaa
                20                  25                  30

Xaa Xaa Xaa Xaa Xaa Xaa Xaa Xaa Xaa Gln Pro Pro Pro Lys
        35                  40                  45

<210> SEQ ID NO 58
<211> LENGTH: 50
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acyl-His
<220> FEATURE:
<221> NAME/KEY: MISC_FEATURE
<222> LOCATION: (4)..(4)
<223> OTHER INFORMATION: can be Gly or Ala
<220> FEATURE:
<221> NAME/KEY: MISC_FEATURE
<222> LOCATION: (5)..(5)
<223> OTHER INFORMATION: can be Val, Ile or Leu
<220> FEATURE:
<221> NAME/KEY: MISC_FEATURE
<222> LOCATION: (8)..(8)
<223> OTHER INFORMATION: can be Asp or Arg
<220> FEATURE:
<221> NAME/KEY: MISC_FEATURE
<222> LOCATION: (9)..(9)
<223> OTHER INFORMATION: can be Ser or Asn
<220> FEATURE:
<221> NAME/KEY: MISC_FEATURE
<222> LOCATION: (11)..(11)
<223> OTHER INFORMATION: can be Ser or Thr
<220> FEATURE:
<221> NAME/KEY: MISC_FEATURE
<222> LOCATION: (13)..(13)
<223> OTHER INFORMATION: can be Leu or Tyr
<220> FEATURE:
<221> NAME/KEY: MISC_FEATURE
<222> LOCATION: (17)..(17)
<223> OTHER INFORMATION: can be Met, Leu or Val
<220> FEATURE:
<221> NAME/KEY: MISC_FEATURE
<222> LOCATION: (19)..(19)
<223> OTHER INFORMATION: can be Ala or Val
<220> FEATURE:
<221> NAME/KEY: MISC_FEATURE
<222> LOCATION: (24)..(24)
<223> OTHER INFORMATION: can be Asn, Gln or Ala
<220> FEATURE:
<221> NAME/KEY: MISC_FEATURE
<222> LOCATION: (25)..(25)
<223> OTHER INFORMATION: can be Trp, Ala or Ser
<220> FEATURE:
<221> NAME/KEY: MISC_FEATURE
<222> LOCATION: (26)..(26)
<223> OTHER INFORMATION: can be Ile or Val
<220> FEATURE:
<221> NAME/KEY: MISC_FEATURE
<222> LOCATION: (27)..(27)
<223> OTHER INFORMATION: can be Leu or Lys
<220> FEATURE:
<221> NAME/KEY: MISC_FEATURE
<222> LOCATION: (28)..(28)
<223> OTHER INFORMATION: can be Lys, Arg, Asn or Gly
<220> FEATURE:
<221> NAME/KEY: MISC_FEATURE
<222> LOCATION: (29)..(29)
<223> OTHER INFORMATION: can be Ala or Gly
<220> FEATURE:
<221> NAME/KEY: MISC_FEATURE
<222> LOCATION: (30)..(30)
<223> OTHER INFORMATION: can be Lys or Arg
<220> FEATURE:

-continued

```
<221> NAME/KEY: MISC_FEATURE
<222> LOCATION: (31)..(31)
<223> OTHER INFORMATION: can be Lys or Arg
<220> FEATURE:
<221> NAME/KEY: MISC_FEATURE
<222> LOCATION: (32)..(32)
<223> OTHER INFORMATION: is a Hydrophilic amino acid
<220> FEATURE:
<221> NAME/KEY: MISC_FEATURE
<222> LOCATION: (33)..(33)
<223> OTHER INFORMATION: is a Lipophilic amino acid
<220> FEATURE:
<221> NAME/KEY: MISC_FEATURE
<222> LOCATION: (34)..(34)
<223> OTHER INFORMATION: is a Lipophilic amino acid
<220> FEATURE:
<221> NAME/KEY: MISC_FEATURE
<222> LOCATION: (35)..(35)
<223> OTHER INFORMATION: is a Hydrophilic amino acid
<220> FEATURE:
<221> NAME/KEY: MISC_FEATURE
<222> LOCATION: (36)..(36)
<223> OTHER INFORMATION: is a Hydrophilic amino acid
<220> FEATURE:
<221> NAME/KEY: MISC_FEATURE
<222> LOCATION: (37)..(37)
<223> OTHER INFORMATION: is a Lipophilic amino acid
<220> FEATURE:
<221> NAME/KEY: MISC_FEATURE
<222> LOCATION: (38)..(38)
<223> OTHER INFORMATION: is a Lipophilic amino acid
<220> FEATURE:
<221> NAME/KEY: MISC_FEATURE
<222> LOCATION: (39)..(39)
<223> OTHER INFORMATION: is a Hydrophilic amino acid
<220> FEATURE:
<221> NAME/KEY: MISC_FEATURE
<222> LOCATION: (40)..(40)
<223> OTHER INFORMATION: is a Hydrophilic amino acid
<220> FEATURE:
<221> NAME/KEY: MISC_FEATURE
<222> LOCATION: (41)..(41)
<223> OTHER INFORMATION: is a Lipophilic amino acid
<220> FEATURE:
<221> NAME/KEY: MISC_FEATURE
<222> LOCATION: (42)..(42)
<223> OTHER INFORMATION: is a Lipophilic amino acid
<220> FEATURE:
<221> NAME/KEY: MISC_FEATURE
<222> LOCATION: (43)..(43)
<223> OTHER INFORMATION: is a Hydrophilic amino acid
<220> FEATURE:
<221> NAME/KEY: MISC_FEATURE
<222> LOCATION: (44)..(44)
<223> OTHER INFORMATION: is a Hydrophilic amino acid
<220> FEATURE:
<221> NAME/KEY: MISC_FEATURE
<222> LOCATION: (45)..(45)
<223> OTHER INFORMATION: is a Lipophilic amino acid
<220> FEATURE:
<221> NAME/KEY: MISC_FEATURE
<222> LOCATION: (50)..(50)
<223> OTHER INFORMATION: Lys(epsilon long acyl)

<400> SEQUENCE: 58

His Ser Asp Xaa Xaa Phe Thr Xaa Xaa Tyr Xaa Arg Xaa Arg Lys Gln
1               5                   10                  15

Xaa Ala Xaa Lys Lys Tyr Leu Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Gln Pro Pro
        35                  40                  45

Pro Lys
    50
```

```
<210> SEQ ID NO 59
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acyl-His
<220> FEATURE:
<221> NAME/KEY: MISC_FEATURE
<222> LOCATION: (4)..(4)
<223> OTHER INFORMATION: can be Gly or Ala
<220> FEATURE:
<221> NAME/KEY: MISC_FEATURE
<222> LOCATION: (5)..(5)
<223> OTHER INFORMATION: can be Val, Ile or Leu
<220> FEATURE:
<221> NAME/KEY: MISC_FEATURE
<222> LOCATION: (8)..(8)
<223> OTHER INFORMATION: can be Asp or Arg
<220> FEATURE:
<221> NAME/KEY: MISC_FEATURE
<222> LOCATION: (9)..(9)
<223> OTHER INFORMATION: can be Ser or Asn
<220> FEATURE:
<221> NAME/KEY: MISC_FEATURE
<222> LOCATION: (11)..(11)
<223> OTHER INFORMATION: can be Ser or Thr
<220> FEATURE:
<221> NAME/KEY: MISC_FEATURE
<222> LOCATION: (13)..(13)
<223> OTHER INFORMATION: can be Leu or Tyr
<220> FEATURE:
<221> NAME/KEY: MISC_FEATURE
<222> LOCATION: (17)..(17)
<223> OTHER INFORMATION: can be Met, Leu or Val
<220> FEATURE:
<221> NAME/KEY: MISC_FEATURE
<222> LOCATION: (19)..(19)
<223> OTHER INFORMATION: can be Ala or Val
<220> FEATURE:
<221> NAME/KEY: MISC_FEATURE
<222> LOCATION: (24)..(24)
<223> OTHER INFORMATION: can be Asn, Gln or Ala
<220> FEATURE:
<221> NAME/KEY: MISC_FEATURE
<222> LOCATION: (25)..(25)
<223> OTHER INFORMATION: can be Trp, Ala or Ser
<220> FEATURE:
<221> NAME/KEY: MISC_FEATURE
<222> LOCATION: (26)..(26)
<223> OTHER INFORMATION: can be Ile or Val
<220> FEATURE:
<221> NAME/KEY: MISC_FEATURE
<222> LOCATION: (27)..(27)
<223> OTHER INFORMATION: can be Leu or Lys
<220> FEATURE:
<221> NAME/KEY: MISC_FEATURE
<222> LOCATION: (28)..(28)
<223> OTHER INFORMATION: can be Lys, Arg, Asn or Gly
<220> FEATURE:
<221> NAME/KEY: MISC_FEATURE
<222> LOCATION: (29)..(29)
<223> OTHER INFORMATION: can be Ala or Gly
<220> FEATURE:
<221> NAME/KEY: MISC_FEATURE
<222> LOCATION: (30)..(30)
<223> OTHER INFORMATION: can be Lys or Arg
<220> FEATURE:
<221> NAME/KEY: MISC_FEATURE
<222> LOCATION: (31)..(31)
<223> OTHER INFORMATION: can be Lys or Arg
<220> FEATURE:
<221> NAME/KEY: MISC_FEATURE
<222> LOCATION: (32)..(32)
<223> OTHER INFORMATION: is a Hydrophilic amino acid
<220> FEATURE:
```

```
<221> NAME/KEY: MISC_FEATURE
<222> LOCATION: (33)..(33)
<223> OTHER INFORMATION: is a Lipophilic amino acid
<220> FEATURE:
<221> NAME/KEY: MISC_FEATURE
<222> LOCATION: (34)..(34)
<223> OTHER INFORMATION: is a Lipophilic amino acid
<220> FEATURE:
<221> NAME/KEY: MISC_FEATURE
<222> LOCATION: (35)..(35)
<223> OTHER INFORMATION: is a Hydrophilic amino acid
<220> FEATURE:
<221> NAME/KEY: MISC_FEATURE
<222> LOCATION: (36)..(36)
<223> OTHER INFORMATION: is a Hydrophilic amino acid
<220> FEATURE:
<221> NAME/KEY: MISC_FEATURE
<222> LOCATION: (37)..(37)
<223> OTHER INFORMATION: is a Lipophilic amino acid
<220> FEATURE:
<221> NAME/KEY: MISC_FEATURE
<222> LOCATION: (41)..(41)
<223> OTHER INFORMATION: Lys(epsilon long acyl)

<400> SEQUENCE: 59

His Ser Asp Xaa Xaa Phe Thr Xaa Xaa Tyr Xaa Arg Xaa Arg Lys Gln
1               5                   10                  15

Xaa Ala Xaa Lys Lys Tyr Leu Xaa Xaa Xaa Xaa Xaa Xaa Xaa Xaa
            20                  25                  30

Xaa Xaa Xaa Xaa Xaa Pro Pro Pro Lys
        35                  40

<210> SEQ ID NO 60
<211> LENGTH: 45
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acyl-His
<220> FEATURE:
<221> NAME/KEY: MISC_FEATURE
<222> LOCATION: (4)..(4)
<223> OTHER INFORMATION: can be Gly or Ala
<220> FEATURE:
<221> NAME/KEY: MISC_FEATURE
<222> LOCATION: (5)..(5)
<223> OTHER INFORMATION: can be Val, Ile or Leu
<220> FEATURE:
<221> NAME/KEY: MISC_FEATURE
<222> LOCATION: (8)..(8)
<223> OTHER INFORMATION: can be Asp or Arg
<220> FEATURE:
<221> NAME/KEY: MISC_FEATURE
<222> LOCATION: (9)..(9)
<223> OTHER INFORMATION: can be Ser or Asn
<220> FEATURE:
<221> NAME/KEY: MISC_FEATURE
<222> LOCATION: (11)..(11)
<223> OTHER INFORMATION: can be Ser or Thr
<220> FEATURE:
<221> NAME/KEY: MISC_FEATURE
<222> LOCATION: (13)..(13)
<223> OTHER INFORMATION: can be Leu or Tyr
<220> FEATURE:
<221> NAME/KEY: MISC_FEATURE
<222> LOCATION: (17)..(17)
<223> OTHER INFORMATION: can be Met, Leu or Val
<220> FEATURE:
<221> NAME/KEY: MISC_FEATURE
<222> LOCATION: (19)..(19)
<223> OTHER INFORMATION: can be Ala or Val
<220> FEATURE:
```

```
<221> NAME/KEY: MISC_FEATURE
<222> LOCATION: (24)..(24)
<223> OTHER INFORMATION: can be Asn, Gln or Ala
<220> FEATURE:
<221> NAME/KEY: MISC_FEATURE
<222> LOCATION: (25)..(25)
<223> OTHER INFORMATION: can be Trp, Ala or Ser
<220> FEATURE:
<221> NAME/KEY: MISC_FEATURE
<222> LOCATION: (26)..(26)
<223> OTHER INFORMATION: can be Ile or Val
<220> FEATURE:
<221> NAME/KEY: MISC_FEATURE
<222> LOCATION: (27)..(27)
<223> OTHER INFORMATION: can be Leu or Lys
<220> FEATURE:
<221> NAME/KEY: MISC_FEATURE
<222> LOCATION: (28)..(28)
<223> OTHER INFORMATION: can be Lys, Arg, Asn or Gly
<220> FEATURE:
<221> NAME/KEY: MISC_FEATURE
<222> LOCATION: (29)..(29)
<223> OTHER INFORMATION: can be Ala or Gly
<220> FEATURE:
<221> NAME/KEY: MISC_FEATURE
<222> LOCATION: (30)..(30)
<223> OTHER INFORMATION: can be Lys or Arg
<220> FEATURE:
<221> NAME/KEY: MISC_FEATURE
<222> LOCATION: (31)..(31)
<223> OTHER INFORMATION: can be Lys or Arg
<220> FEATURE:
<221> NAME/KEY: MISC_FEATURE
<222> LOCATION: (32)..(32)
<223> OTHER INFORMATION: is a Hydrophilic amino acid
<220> FEATURE:
<221> NAME/KEY: MISC_FEATURE
<222> LOCATION: (33)..(33)
<223> OTHER INFORMATION: is a Lipophilic amino acid
<220> FEATURE:
<221> NAME/KEY: MISC_FEATURE
<222> LOCATION: (34)..(34)
<223> OTHER INFORMATION: is a Lipophilic amino acid
<220> FEATURE:
<221> NAME/KEY: MISC_FEATURE
<222> LOCATION: (35)..(35)
<223> OTHER INFORMATION: is a Hydrophilic amino acid
<220> FEATURE:
<221> NAME/KEY: MISC_FEATURE
<222> LOCATION: (36)..(36)
<223> OTHER INFORMATION: is a Hydrophilic amino acid
<220> FEATURE:
<221> NAME/KEY: MISC_FEATURE
<222> LOCATION: (37)..(37)
<223> OTHER INFORMATION: is a Lipophilic amino acid
<220> FEATURE:
<221> NAME/KEY: MISC_FEATURE
<222> LOCATION: (38)..(38)
<223> OTHER INFORMATION: is a Lipophilic amino acid
<220> FEATURE:
<221> NAME/KEY: MISC_FEATURE
<222> LOCATION: (39)..(39)
<223> OTHER INFORMATION: is a Hydrophilic amino acid
<220> FEATURE:
<221> NAME/KEY: MISC_FEATURE
<222> LOCATION: (40)..(40)
<223> OTHER INFORMATION: is a Hydrophilic amino acid
<220> FEATURE:
<221> NAME/KEY: MISC_FEATURE
<222> LOCATION: (41)..(41)
<223> OTHER INFORMATION: is a Lipophilic amino acid
<220> FEATURE:
<221> NAME/KEY: MISC_FEATURE
<222> LOCATION: (45)..(45)
<223> OTHER INFORMATION: Lys(epsilon long acyl)

<400> SEQUENCE: 60

His Ser Asp Xaa Xaa Phe Thr Xaa Xaa Tyr Xaa Arg Xaa Arg Lys Gln
```

```
            1               5                  10                  15
Xaa Ala Xaa Lys Lys Tyr Leu Xaa Xaa Xaa Xaa Xaa Xaa Xaa Xaa
                20                  25                  30
Xaa Xaa Xaa Xaa Xaa Xaa Xaa Xaa Xaa Pro Pro Pro Lys
        35                  40                  45
```

```
<210> SEQ ID NO 61
<211> LENGTH: 49
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acyl-His
<220> FEATURE:
<221> NAME/KEY: MISC_FEATURE
<222> LOCATION: (4)..(4)
<223> OTHER INFORMATION: can be Gly or Ala
<220> FEATURE:
<221> NAME/KEY: MISC_FEATURE
<222> LOCATION: (5)..(5)
<223> OTHER INFORMATION: can be Val, Ile or Leu
<220> FEATURE:
<221> NAME/KEY: MISC_FEATURE
<222> LOCATION: (8)..(8)
<223> OTHER INFORMATION: can be Asp or Arg
<220> FEATURE:
<221> NAME/KEY: MISC_FEATURE
<222> LOCATION: (9)..(9)
<223> OTHER INFORMATION: can be Ser or Asn
<220> FEATURE:
<221> NAME/KEY: MISC_FEATURE
<222> LOCATION: (11)..(11)
<223> OTHER INFORMATION: can be Ser or Thr
<220> FEATURE:
<221> NAME/KEY: MISC_FEATURE
<222> LOCATION: (13)..(13)
<223> OTHER INFORMATION: can be Leu or Tyr
<220> FEATURE:
<221> NAME/KEY: MISC_FEATURE
<222> LOCATION: (17)..(17)
<223> OTHER INFORMATION: can be Met, Leu or Val
<220> FEATURE:
<221> NAME/KEY: MISC_FEATURE
<222> LOCATION: (19)..(19)
<223> OTHER INFORMATION: can be Ala or Val
<220> FEATURE:
<221> NAME/KEY: MISC_FEATURE
<222> LOCATION: (24)..(24)
<223> OTHER INFORMATION: can be Asn, Gln or Ala
<220> FEATURE:
<221> NAME/KEY: MISC_FEATURE
<222> LOCATION: (25)..(25)
<223> OTHER INFORMATION: can be Trp, Ala or Ser
<220> FEATURE:
<221> NAME/KEY: MISC_FEATURE
<222> LOCATION: (26)..(26)
<223> OTHER INFORMATION: can be Ile or Val
<220> FEATURE:
<221> NAME/KEY: MISC_FEATURE
<222> LOCATION: (27)..(27)
<223> OTHER INFORMATION: can be Leu or Lys
<220> FEATURE:
<221> NAME/KEY: MISC_FEATURE
<222> LOCATION: (28)..(28)
<223> OTHER INFORMATION: can be Lys, Arg, Asn or Gly
<220> FEATURE:
<221> NAME/KEY: MISC_FEATURE
<222> LOCATION: (29)..(29)
<223> OTHER INFORMATION: can be Ala or Gly
<220> FEATURE:
<221> NAME/KEY: MISC_FEATURE
<222> LOCATION: (30)..(30)
<223> OTHER INFORMATION: can be Lys or Arg
```

```
<220> FEATURE:
<221> NAME/KEY: MISC_FEATURE
<222> LOCATION: (31)..(31)
<223> OTHER INFORMATION: can be Lys or Arg
<220> FEATURE:
<221> NAME/KEY: MISC_FEATURE
<222> LOCATION: (32)..(32)
<223> OTHER INFORMATION: is a Hydrophilic amino acid
<220> FEATURE:
<221> NAME/KEY: MISC_FEATURE
<222> LOCATION: (33)..(33)
<223> OTHER INFORMATION: is a Lipophilic amino acid
<220> FEATURE:
<221> NAME/KEY: MISC_FEATURE
<222> LOCATION: (34)..(34)
<223> OTHER INFORMATION: is a Lipophilic amino acid
<220> FEATURE:
<221> NAME/KEY: MISC_FEATURE
<222> LOCATION: (35)..(35)
<223> OTHER INFORMATION: is a Hydrophilic amino acid
<220> FEATURE:
<221> NAME/KEY: MISC_FEATURE
<222> LOCATION: (36)..(36)
<223> OTHER INFORMATION: is a Hydrophilic amino acid
<220> FEATURE:
<221> NAME/KEY: MISC_FEATURE
<222> LOCATION: (37)..(37)
<223> OTHER INFORMATION: is a Lipophilic amino acid
<220> FEATURE:
<221> NAME/KEY: MISC_FEATURE
<222> LOCATION: (38)..(38)
<223> OTHER INFORMATION: is a Lipophilic amino acid
<220> FEATURE:
<221> NAME/KEY: MISC_FEATURE
<222> LOCATION: (39)..(39)
<223> OTHER INFORMATION: is a Hydrophilic amino acid
<220> FEATURE:
<221> NAME/KEY: MISC_FEATURE
<222> LOCATION: (40)..(40)
<223> OTHER INFORMATION: is a Hydrophilic amino acid
<220> FEATURE:
<221> NAME/KEY: MISC_FEATURE
<222> LOCATION: (41)..(41)
<223> OTHER INFORMATION: is a Lipophilic amino acid
<220> FEATURE:
<221> NAME/KEY: MISC_FEATURE
<222> LOCATION: (42)..(42)
<223> OTHER INFORMATION: is a Lipophilic amino acid
<220> FEATURE:
<221> NAME/KEY: MISC_FEATURE
<222> LOCATION: (43)..(43)
<223> OTHER INFORMATION: is a Hydrophilic amino acid
<220> FEATURE:
<221> NAME/KEY: MISC_FEATURE
<222> LOCATION: (44)..(44)
<223> OTHER INFORMATION: is a Hydrophilic amino acid
<220> FEATURE:
<221> NAME/KEY: MISC_FEATURE
<222> LOCATION: (45)..(45)
<223> OTHER INFORMATION: is a Lipophilic amino acid
<220> FEATURE:
<221> NAME/KEY: MISC_FEATURE
<222> LOCATION: (49)..(49)
<223> OTHER INFORMATION: Lys(epsilon long acyl)

<400> SEQUENCE: 61

His Ser Asp Xaa Xaa Phe Thr Xaa Xaa Tyr Xaa Arg Xaa Arg Lys Gln
1               5                   10                  15

Xaa Ala Xaa Lys Lys Tyr Leu Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Pro Pro Pro
        35                  40                  45

Lys
```

```
<210> SEQ ID NO 62
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acyl-His
<220> FEATURE:
<221> NAME/KEY: MISC_FEATURE
<222> LOCATION: (4)..(4)
<223> OTHER INFORMATION: can be Gly or Ala
<220> FEATURE:
<221> NAME/KEY: MISC_FEATURE
<222> LOCATION: (5)..(5)
<223> OTHER INFORMATION: can be Val, Ile or Leu
<220> FEATURE:
<221> NAME/KEY: MISC_FEATURE
<222> LOCATION: (8)..(8)
<223> OTHER INFORMATION: can be Asp or Arg
<220> FEATURE:
<221> NAME/KEY: MISC_FEATURE
<222> LOCATION: (9)..(9)
<223> OTHER INFORMATION: can be Ser or Asn
<220> FEATURE:
<221> NAME/KEY: MISC_FEATURE
<222> LOCATION: (11)..(11)
<223> OTHER INFORMATION: can be Ser or Thr
<220> FEATURE:
<221> NAME/KEY: MISC_FEATURE
<222> LOCATION: (13)..(13)
<223> OTHER INFORMATION: can be Leu or Tyr
<220> FEATURE:
<221> NAME/KEY: MISC_FEATURE
<222> LOCATION: (17)..(17)
<223> OTHER INFORMATION: can be Met, Leu or Val
<220> FEATURE:
<221> NAME/KEY: MISC_FEATURE
<222> LOCATION: (19)..(19)
<223> OTHER INFORMATION: can be Ala or Val
<220> FEATURE:
<221> NAME/KEY: MISC_FEATURE
<222> LOCATION: (24)..(24)
<223> OTHER INFORMATION: can be Asn, Gln or Ala
<220> FEATURE:
<221> NAME/KEY: MISC_FEATURE
<222> LOCATION: (25)..(25)
<223> OTHER INFORMATION: can be Trp, Ala or Ser
<220> FEATURE:
<221> NAME/KEY: MISC_FEATURE
<222> LOCATION: (26)..(26)
<223> OTHER INFORMATION: can be Ile or Val
<220> FEATURE:
<221> NAME/KEY: MISC_FEATURE
<222> LOCATION: (27)..(27)
<223> OTHER INFORMATION: can be Leu or Lys
<220> FEATURE:
<221> NAME/KEY: MISC_FEATURE
<222> LOCATION: (28)..(28)
<223> OTHER INFORMATION: can be Lys, Arg, Asn or Gly
<220> FEATURE:
<221> NAME/KEY: MISC_FEATURE
<222> LOCATION: (29)..(29)
<223> OTHER INFORMATION: can be Ala or Gly
<220> FEATURE:
<221> NAME/KEY: MISC_FEATURE
<222> LOCATION: (30)..(30)
<223> OTHER INFORMATION: can be Lys or Arg
<220> FEATURE:
<221> NAME/KEY: MISC_FEATURE
<222> LOCATION: (31)..(31)
<223> OTHER INFORMATION: can be Lys or Arg
<220> FEATURE:
<221> NAME/KEY: MISC_FEATURE
<222> LOCATION: (32)..(32)
<223> OTHER INFORMATION: is a Hydrophilic amino acid
<220> FEATURE:
```

```
<221> NAME/KEY: MISC_FEATURE
<222> LOCATION: (33)..(33)
<223> OTHER INFORMATION: is a Lipophilic amino acid
<220> FEATURE:
<221> NAME/KEY: MISC_FEATURE
<222> LOCATION: (34)..(34)
<223> OTHER INFORMATION: is a Lipophilic amino acid
<220> FEATURE:
<221> NAME/KEY: MISC_FEATURE
<222> LOCATION: (35)..(35)
<223> OTHER INFORMATION: is a Hydrophilic amino acid
<220> FEATURE:
<221> NAME/KEY: MISC_FEATURE
<222> LOCATION: (36)..(36)
<223> OTHER INFORMATION: is a Hydrophilic amino acid
<220> FEATURE:
<221> NAME/KEY: MISC_FEATURE
<222> LOCATION: (37)..(37)
<223> OTHER INFORMATION: is a Lipophilic amino acid
<220> FEATURE:
<221> NAME/KEY: MISC_FEATURE
<222> LOCATION: (38)..(38)
<223> OTHER INFORMATION: Lys(epsilon long acyl)

<400> SEQUENCE: 62

His Ser Asp Xaa Xaa Phe Thr Xaa Xaa Tyr Xaa Arg Xaa Arg Lys Gln
1               5                   10                  15

Xaa Ala Xaa Lys Lys Tyr Leu Xaa Xaa Xaa Xaa Xaa Xaa Xaa Xaa
            20                  25                  30

Xaa Xaa Xaa Xaa Xaa Lys
        35

<210> SEQ ID NO 63
<211> LENGTH: 42
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acyl-His
<220> FEATURE:
<221> NAME/KEY: MISC_FEATURE
<222> LOCATION: (4)..(4)
<223> OTHER INFORMATION: can be Gly or Ala
<220> FEATURE:
<221> NAME/KEY: MISC_FEATURE
<222> LOCATION: (5)..(5)
<223> OTHER INFORMATION: can be Val, Ile or Leu
<220> FEATURE:
<221> NAME/KEY: MISC_FEATURE
<222> LOCATION: (8)..(8)
<223> OTHER INFORMATION: can be Asp or Arg
<220> FEATURE:
<221> NAME/KEY: MISC_FEATURE
<222> LOCATION: (9)..(9)
<223> OTHER INFORMATION: can be Ser or Asn
<220> FEATURE:
<221> NAME/KEY: MISC_FEATURE
<222> LOCATION: (11)..(11)
<223> OTHER INFORMATION: can be Ser or Thr
<220> FEATURE:
<221> NAME/KEY: MISC_FEATURE
<222> LOCATION: (13)..(13)
<223> OTHER INFORMATION: can be Leu or Tyr
<220> FEATURE:
<221> NAME/KEY: MISC_FEATURE
<222> LOCATION: (17)..(17)
<223> OTHER INFORMATION: can be Met, Leu or Val
<220> FEATURE:
<221> NAME/KEY: MISC_FEATURE
<222> LOCATION: (19)..(19)
<223> OTHER INFORMATION: can be Ala or Val
<220> FEATURE:
```

```
<221> NAME/KEY: MISC_FEATURE
<222> LOCATION: (24)..(24)
<223> OTHER INFORMATION: can be Asn, Gln or Ala
<220> FEATURE:
<221> NAME/KEY: MISC_FEATURE
<222> LOCATION: (25)..(25)
<223> OTHER INFORMATION: can be Trp, Ala or Ser
<220> FEATURE:
<221> NAME/KEY: MISC_FEATURE
<222> LOCATION: (26)..(26)
<223> OTHER INFORMATION: can be Ile or Val
<220> FEATURE:
<221> NAME/KEY: MISC_FEATURE
<222> LOCATION: (27)..(27)
<223> OTHER INFORMATION: can be Leu or Lys
<220> FEATURE:
<221> NAME/KEY: MISC_FEATURE
<222> LOCATION: (28)..(28)
<223> OTHER INFORMATION: can be Lys, Arg, Asn or Gly
<220> FEATURE:
<221> NAME/KEY: MISC_FEATURE
<222> LOCATION: (29)..(29)
<223> OTHER INFORMATION: can be Ala or Gly
<220> FEATURE:
<221> NAME/KEY: MISC_FEATURE
<222> LOCATION: (30)..(30)
<223> OTHER INFORMATION: can be Lys or Arg
<220> FEATURE:
<221> NAME/KEY: MISC_FEATURE
<222> LOCATION: (31)..(31)
<223> OTHER INFORMATION: can be Lys or Arg
<220> FEATURE:
<221> NAME/KEY: MISC_FEATURE
<222> LOCATION: (32)..(32)
<223> OTHER INFORMATION: is a Hydrophilic amino acid
<220> FEATURE:
<221> NAME/KEY: MISC_FEATURE
<222> LOCATION: (33)..(33)
<223> OTHER INFORMATION: is a Lipophilic amino acid
<220> FEATURE:
<221> NAME/KEY: MISC_FEATURE
<222> LOCATION: (34)..(34)
<223> OTHER INFORMATION: is a Lipophilic amino acid
<220> FEATURE:
<221> NAME/KEY: MISC_FEATURE
<222> LOCATION: (35)..(35)
<223> OTHER INFORMATION: is a Hydrophilic amino acid
<220> FEATURE:
<221> NAME/KEY: MISC_FEATURE
<222> LOCATION: (36)..(36)
<223> OTHER INFORMATION: is a Hydrophilic amino acid
<220> FEATURE:
<221> NAME/KEY: MISC_FEATURE
<222> LOCATION: (37)..(37)
<223> OTHER INFORMATION: is a Lipophilic amino acid
<220> FEATURE:
<221> NAME/KEY: MISC_FEATURE
<222> LOCATION: (38)..(38)
<223> OTHER INFORMATION: is a Lipophilic amino acid
<220> FEATURE:
<221> NAME/KEY: MISC_FEATURE
<222> LOCATION: (39)..(39)
<223> OTHER INFORMATION: is a Hydrophilic amino acid
<220> FEATURE:
<221> NAME/KEY: MISC_FEATURE
<222> LOCATION: (40)..(40)
<223> OTHER INFORMATION: is a Hydrophilic amino acid
<220> FEATURE:
<221> NAME/KEY: MISC_FEATURE
<222> LOCATION: (41)..(41)
<223> OTHER INFORMATION: is a Lipophilic amino acid
<220> FEATURE:
<221> NAME/KEY: MISC_FEATURE
<222> LOCATION: (42)..(42)
<223> OTHER INFORMATION: Lys(epsilon long acyl)

<400> SEQUENCE: 63

His Ser Asp Xaa Xaa Phe Thr Xaa Xaa Tyr Xaa Arg Xaa Arg Lys Gln
```

```
            1               5                  10                 15
Xaa Ala Xaa Lys Lys Tyr Leu Xaa Xaa Xaa Xaa Xaa Xaa Xaa Xaa
            20                 25                 30

Xaa Xaa Xaa Xaa Xaa Xaa Xaa Xaa Xaa Lys
        35                 40
```

<210> SEQ ID NO 64
<211> LENGTH: 46
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acyl-His
<220> FEATURE:
<221> NAME/KEY: MISC_FEATURE
<222> LOCATION: (4)..(4)
<223> OTHER INFORMATION: can be Gly or Ala
<220> FEATURE:
<221> NAME/KEY: MISC_FEATURE
<222> LOCATION: (5)..(5)
<223> OTHER INFORMATION: can be Val, Ile or Leu
<220> FEATURE:
<221> NAME/KEY: MISC_FEATURE
<222> LOCATION: (8)..(8)
<223> OTHER INFORMATION: can be Asp or Arg
<220> FEATURE:
<221> NAME/KEY: MISC_FEATURE
<222> LOCATION: (9)..(9)
<223> OTHER INFORMATION: can be Ser or Asn
<220> FEATURE:
<221> NAME/KEY: MISC_FEATURE
<222> LOCATION: (11)..(11)
<223> OTHER INFORMATION: can be Ser or Thr
<220> FEATURE:
<221> NAME/KEY: MISC_FEATURE
<222> LOCATION: (13)..(13)
<223> OTHER INFORMATION: can be Leu or Tyr
<220> FEATURE:
<221> NAME/KEY: MISC_FEATURE
<222> LOCATION: (17)..(17)
<223> OTHER INFORMATION: can be Met, Leu or Val
<220> FEATURE:
<221> NAME/KEY: MISC_FEATURE
<222> LOCATION: (19)..(19)
<223> OTHER INFORMATION: can be Ala or Val
<220> FEATURE:
<221> NAME/KEY: MISC_FEATURE
<222> LOCATION: (24)..(24)
<223> OTHER INFORMATION: can be Asn, Gln or Ala
<220> FEATURE:
<221> NAME/KEY: MISC_FEATURE
<222> LOCATION: (25)..(25)
<223> OTHER INFORMATION: can be Trp, Ala or Ser
<220> FEATURE:
<221> NAME/KEY: MISC_FEATURE
<222> LOCATION: (26)..(26)
<223> OTHER INFORMATION: can be Ile or Val
<220> FEATURE:
<221> NAME/KEY: MISC_FEATURE
<222> LOCATION: (27)..(27)
<223> OTHER INFORMATION: can be Leu or Lys
<220> FEATURE:
<221> NAME/KEY: MISC_FEATURE
<222> LOCATION: (28)..(28)
<223> OTHER INFORMATION: can be Lys, Arg, Asn or Gly
<220> FEATURE:
<221> NAME/KEY: MISC_FEATURE
<222> LOCATION: (29)..(29)
<223> OTHER INFORMATION: can be Ala or Gly
<220> FEATURE:
<221> NAME/KEY: MISC_FEATURE
<222> LOCATION: (30)..(30)
<223> OTHER INFORMATION: can be Lys or Arg

```
<220> FEATURE:
<221> NAME/KEY: MISC_FEATURE
<222> LOCATION: (31)..(31)
<223> OTHER INFORMATION: can be Lys or Arg
<220> FEATURE:
<221> NAME/KEY: MISC_FEATURE
<222> LOCATION: (32)..(32)
<223> OTHER INFORMATION: is a Hydrophilic amino acid
<220> FEATURE:
<221> NAME/KEY: MISC_FEATURE
<222> LOCATION: (33)..(33)
<223> OTHER INFORMATION: is a Lipophilic amino acid
<220> FEATURE:
<221> NAME/KEY: MISC_FEATURE
<222> LOCATION: (34)..(34)
<223> OTHER INFORMATION: is a Lipophilic amino acid
<220> FEATURE:
<221> NAME/KEY: MISC_FEATURE
<222> LOCATION: (35)..(35)
<223> OTHER INFORMATION: is a Hydrophilic amino acid
<220> FEATURE:
<221> NAME/KEY: MISC_FEATURE
<222> LOCATION: (36)..(36)
<223> OTHER INFORMATION: is a Hydrophilic amino acid
<220> FEATURE:
<221> NAME/KEY: MISC_FEATURE
<222> LOCATION: (37)..(37)
<223> OTHER INFORMATION: is a Lipophilic amino acid
<220> FEATURE:
<221> NAME/KEY: MISC_FEATURE
<222> LOCATION: (38)..(38)
<223> OTHER INFORMATION: is a Lipophilic amino acid
<220> FEATURE:
<221> NAME/KEY: MISC_FEATURE
<222> LOCATION: (39)..(39)
<223> OTHER INFORMATION: is a Hydrophilic amino acid
<220> FEATURE:
<221> NAME/KEY: MISC_FEATURE
<222> LOCATION: (40)..(40)
<223> OTHER INFORMATION: is a Hydrophilic amino acid
<220> FEATURE:
<221> NAME/KEY: MISC_FEATURE
<222> LOCATION: (41)..(41)
<223> OTHER INFORMATION: is a Lipophilic amino acid
<220> FEATURE:
<221> NAME/KEY: MISC_FEATURE
<222> LOCATION: (42)..(42)
<223> OTHER INFORMATION: is a Lipophilic amino acid
<220> FEATURE:
<221> NAME/KEY: MISC_FEATURE
<222> LOCATION: (43)..(43)
<223> OTHER INFORMATION: is a Hydrophilic amino acid
<220> FEATURE:
<221> NAME/KEY: MISC_FEATURE
<222> LOCATION: (44)..(44)
<223> OTHER INFORMATION: is a Hydrophilic amino acid
<220> FEATURE:
<221> NAME/KEY: MISC_FEATURE
<222> LOCATION: (45)..(45)
<223> OTHER INFORMATION: is a Lipophilic amino acid
<220> FEATURE:
<221> NAME/KEY: MISC_FEATURE
<222> LOCATION: (46)..(46)
<223> OTHER INFORMATION: Lys(epsilon long acyl)

<400> SEQUENCE: 64

His Ser Asp Xaa Xaa Phe Thr Xaa Xaa Tyr Xaa Arg Xaa Arg Lys Gln
1               5                   10                  15

Xaa Ala Xaa Lys Lys Tyr Leu Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Lys
            35                  40                  45
```